United States Patent
Murphy et al.

(10) Patent No.: US 12,178,716 B2
(45) Date of Patent: Dec. 31, 2024

(54) SYSTEM AND METHOD TO ALTER BONE GROWTH IN A TARGETED SPATIAL REGION FOR THE USE WITH IMPLANTS

(71) Applicant: Intelligent Implants Limited, Cork (IE)

(72) Inventors: Rory Kenneth John Murphy, Phoenix, AZ (US); Erik Robert Zellmer, Gottenburg (SE); John Michael Zellmer, Gottenburg (SE)

(73) Assignee: Intelligent Implants Limited, Cork (IE)

( * ) Notice: Subject to any disclaimer, the term of this patent is extended or adjusted under 35 U.S.C. 154(b) by 0 days.

(21) Appl. No.: 18/097,211

(22) Filed: Jan. 14, 2023

(65) Prior Publication Data

US 2023/0248533 A1 Aug. 10, 2023

Related U.S. Application Data

(63) Continuation of application No. 16/592,523, filed on Oct. 3, 2019, now Pat. No. 11,576,789.

(Continued)

(51) Int. Cl.
*A61N 1/00* (2006.01)
*A61F 2/44* (2006.01)
(Continued)

(52) U.S. Cl.
CPC .......... *A61F 2/4455* (2013.01); *A61N 1/0551* (2013.01); *A61N 1/326* (2013.01);
(Continued)

(58) Field of Classification Search
CPC ............ A61F 2/4455; A61F 2002/2821; A61F 2310/00149; A61F 2/482;
(Continued)

(56) References Cited

U.S. PATENT DOCUMENTS 3,842,841 A   10/1974   Brighton et al.
4,175,565 A   11/1979   Chiarenza et al.
(Continued)

FOREIGN PATENT DOCUMENTS

WO   2013188380 A1   12/2013
WO   2014089299 A3   10/2014

OTHER PUBLICATIONS

Laughner Ji, et al. (2013) A Fully Implantable Pacemaker for the Mouse: From Battery to Wireless Power. PLOS ONE 8(10): e76291. https://doi.org/10.1371/journal.pone.0076291, Oct. 23, 2013.

(Continued)

*Primary Examiner* — Scott M. Getzow
(74) *Attorney, Agent, or Firm* — Alpine Patents LLC; Brian Van Osdol

(57) ABSTRACT

A system and method for altering bone growth on and within an orthopedic implant that includes an implant body; a plurality of electrodes, wherein each electrode is at least partially embedded in the implant body, and comprises: a set of primary electrodes comprising at least one electrode, wherein a non-embedded segment of each primary electrode is proximal to a bone growth region, a set of secondary electrodes comprising at least one electrode, wherein a non-embedded segment of each secondary electrode is distal to the bone growth region, and wherein the plurality of electrodes are configured to function in a stimulation operating mode, such that a subset of primary electrodes function as cathodes and a subset of secondary electrodes function as anodes; a control system comprising a processor, and circuitry that connects to the plurality of electrodes; and a power system.

21 Claims, 14 Drawing Sheets

Related U.S. Application Data

(60) Provisional application No. 62/740,853, filed on Oct. 3, 2018, provisional application No. 62/740,839, filed on Oct. 3, 2018.

(51) Int. Cl.
  *A61N 1/05* (2006.01)
  *A61N 1/32* (2006.01)
  *A61N 1/36* (2006.01)
  *A61N 1/378* (2006.01)
  *A61F 2/28* (2006.01)
  *A61L 27/06* (2006.01)

(52) U.S. Cl.
  CPC ......... *A61N 1/36062* (2017.08); *A61N 1/378* (2013.01); *A61N 1/3787* (2013.01); *A61F 2002/2821* (2013.01); *A61F 2310/00149* (2013.01); *A61L 27/06* (2013.01)

(58) Field of Classification Search
  CPC ...... A61F 2002/30593; A61F 2002/448; A61F 2/4465; A61F 2/447; A61N 1/0551; A61N 1/326; A61N 1/36062; A61N 1/378; A61N 1/3787; A61L 27/06
  See application file for complete search history.

(56) References Cited

U.S. PATENT DOCUMENTS

| | | |
|---|---|---|
| 4,313,438 A | 2/1982 | Greatbatch |
| 4,690,144 A | 9/1987 | Rise et al. |
| 4,690,166 A | 9/1987 | Howeth |
| 5,056,518 A | 10/1991 | Pethica et al. |
| 5,330,477 A | 7/1994 | Crook |
| 5,358,514 A | 10/1994 | Schulman et al. |
| 5,441,527 A | 8/1995 | Erickson et al. |
| 5,458,627 A | 10/1995 | Baranowski, Jr. et al. |
| 5,565,005 A | 10/1996 | Erickson et al. |
| 5,974,342 A | 10/1999 | Petrofsky |
| 5,989,289 A | 11/1999 | Coates et al. |
| 6,120,502 A | 9/2000 | Michelson |
| 6,292,699 B1 | 9/2001 | Simon et al. |
| 6,400,990 B1 | 6/2002 | Silvian |
| 6,582,467 B1 | 6/2003 | Teitelbaum et al. |
| 6,605,089 B1 | 8/2003 | Michelson |
| 7,104,986 B2 | 9/2006 | Hovda et al. |
| 7,309,338 B2 | 12/2007 | Cragg |
| 7,324,852 B2 | 1/2008 | Barolat et al. |
| 7,359,755 B2 | 4/2008 | Jones et al. |
| 7,455,672 B2 | 11/2008 | Michelson |
| 7,578,819 B2 | 8/2009 | Bleich et al. |
| 7,935,116 B2 | 5/2011 | Michelson |
| 8,014,873 B2 | 9/2011 | Jones et al. |
| 8,078,282 B2 | 12/2011 | Nycz |
| 8,078,283 B2 | 12/2011 | Cowan et al. |
| 8,206,387 B2 | 6/2012 | Michelson |
| 8,463,401 B2 | 6/2013 | Jones et al. |
| 8,666,471 B2 | 3/2014 | Rogers et al. |
| 8,718,777 B2 | 5/2014 | Lowry et al. |
| 8,740,879 B2 | 6/2014 | Martinson et al. |
| 8,771,360 B2 | 7/2014 | Jimenez et al. |
| 8,838,249 B2 | 9/2014 | Nycz |
| 8,903,502 B2 | 12/2014 | Perryman et al. |
| 10,292,831 B2 | 5/2019 | Zellmer et al. |
| 10,617,880 B2 | 4/2020 | Zellmer et al. |
| 11,058,549 B2 | 7/2021 | Zellmer et al. |
| 11,097,096 B2 | 8/2021 | Linden et al. |
| 11,395,744 B2 | 7/2022 | Zellmer et al. |
| 11,471,297 B2 | 10/2022 | Zellmer et al. |
| 11,484,722 B2 | 11/2022 | Zellmer et al. |
| 11,576,789 B2 | 2/2023 | Murphy et al. |
| 2003/0078634 A1 | 4/2003 | Schulman et al. |
| 2004/0249373 A1 | 12/2004 | Gronemeyer et al. |
| 2005/0033393 A1 | 2/2005 | Daglow |
| 2005/0216702 A1 | 9/2005 | Paolucci et al. |
| 2007/0250045 A1 | 10/2007 | Trieu |
| 2008/0039901 A1 | 2/2008 | Kronberg et al. |
| 2008/0294211 A1 | 11/2008 | Moffitt |
| 2008/0300660 A1 | 12/2008 | John |
| 2009/0062886 A1 | 3/2009 | O'Handley et al. |
| 2010/0168829 A1 | 7/2010 | Schwartz et al. |
| 2010/0204551 A1 | 8/2010 | Roche |
| 2010/0292756 A1 | 11/2010 | Schneider |
| 2011/0009728 A1 | 1/2011 | Schouenborg |
| 2011/0087315 A1 | 4/2011 | Richardson-Burns et al. |
| 2011/0092948 A1 | 4/2011 | Shachar et al. |
| 2011/0301716 A1 | 12/2011 | Sirivisoot et al. |
| 2013/0150970 A1 | 6/2013 | Thaiyananthan |
| 2013/0165991 A1 | 6/2013 | Kim et al. |
| 2013/0296940 A1 | 11/2013 | Northcutt et al. |
| 2014/0114382 A1 | 4/2014 | Kim |
| 2014/0133123 A1 | 5/2014 | Prasannakumar et al. |
| 2014/0275847 A1 | 9/2014 | Perryman et al. |
| 2014/0277260 A1 | 9/2014 | Khalil et al. |
| 2014/0371823 A1 | 12/2014 | Mashiach et al. |
| 2015/0018728 A1 | 1/2015 | Gross et al. |
| 2015/0134061 A1 | 5/2015 | Friis et al. |
| 2015/0187320 A1 | 7/2015 | Ren |
| 2016/0270927 A1* | 9/2016 | Zellmer ................ A61N 1/326 |
| 2017/0007420 A1 | 1/2017 | Stevenson et al. |
| 2017/0157407 A1 | 6/2017 | Zellmer et al. |
| 2017/0246448 A1 | 8/2017 | Lenoble et al. |
| 2018/0078774 A1 | 3/2018 | Strommer et al. |
| 2018/0208992 A1 | 7/2018 | Langevin et al. |
| 2018/0310964 A1 | 11/2018 | Stevenson et al. |
| 2020/0297513 A1 | 9/2020 | Zellmer et al. |
| 2020/0352723 A1 | 11/2020 | Jimenez et al. |
| 2021/0128919 A1 | 5/2021 | Zellmer et al. |
| 2022/0305258 A1 | 9/2022 | Zellmer et al. |
| 2022/0370208 A1 | 11/2022 | Zellmer et al. |
| 2023/0067388 A1 | 3/2023 | Zellmer et al. |
| 2023/0082022 A1 | 3/2023 | Zellmer et al. |

OTHER PUBLICATIONS

WIPO European Searching Authority, "PCT2016000482 WO Search And Opinion", Jul. 7, 2016.

* cited by examiner

Positioning of electrodes. S110

Creating a polarity within a subset of the electrodes. S120

FIGURE 14

SYSTEM AND METHOD TO ALTER BONE GROWTH IN A TARGETED SPATIAL REGION FOR THE USE WITH IMPLANTS

CROSS-REFERENCE TO RELATED APPLICATIONS

This Application is a Continuation Application of U.S. patent application Ser. No. 16/592,523, filed on 3 Oct. 2019, which claims the benefit of U.S. Provisional Application No. 62/740,839, filed on 3 Oct. 2018, and U.S. Provisional Application No. 62/740,853, filed on 3 Oct. 2018, all of which are incorporated in their entireties by this reference.

TECHNICAL FIELD

This invention relates generally to the field of bone growth, and more specifically, to a new and useful system and method to alter bone growth in a specific spatial region.

BACKGROUND

Spinal fusion is one of the most commonly performed surgical procedures within the US and in Europe. The goal of spinal fusion surgery is to introduce bone growth between two or more vertebrae, fusing them into a single, continuous unit. Spinal fusion surgery is performed in the lumbar, cervical and thoracic regions, and fusions within each region are associated with a different set of complications. Even so, most complications following spinal fusion can be generalized into two broad categories: non-fusions, where the vertebrae are not fused into a singular unit due to insufficient bone formation within the fusion space; heterotopic ossification, where bone growth damages or impinges on tissue causing harm or discomfort to the patient. Examples of heterotopic ossification includes: Anterior osteophyte formation causing mass effect on the esophagus leading difficulty of swallowing (cervical fusions); ossification of the posterior longitudinal ligament; and formation of posterior osteophyte and/or other excessive posterior bone growth pressuring the spinal cord and/or spinal nerves.

Many contemporary spinal fusion hardware and biologics include designs to address the problems associated with non-unions, with little regard to heterotopic ossification. For example, commonly used biologics, particularly recombinant human bone morphogenetic protein (rhBMP-2), have been used to reduce non-fusion rates by increasing bone formation in the fusion space and the volume surrounding it. While clinically proven to decrease non-unions, numerous studies have shown that the biologic causes a host of side effects including but not limited to cancer, tissue swelling, growth of benign tissue, teratogenicity, pathological heterotopic ossification, nerve injury and spinal cord injury. While not all side effects caused by rhBMP-2 are related to heterotopic ossification, many are. As such, the biologic represents an illustrating example of how, nonspecific, unguided osteoinduction can be harmful to a patient and the delicate balance between increasing fusion rates and avoiding heterotopic ossification.

A second method utilized in reducing non-union rates is electrical stimulation. When mechanical stress is exerted on bone, an electric field is created. In the body, this electrical field constitutes a signal causing a physiological response resulting in osteoinduction or osteolysis. Consequently, it is possible to cause osteoinduction or osteolysis by introducing an electrical field in the volume within and surrounding a segment of bone. In volumes where the current density is above a certain threshold, osteoinduction is achieved if the polarity of the field in the region is electronegative while bone in regions where the field is electropositive undergoes osteolysis.

With the advent of electrically stimulated bone growth, there is an increasing need to fine tune the methods of bone growth such that osteoinduction and osteolysis occur more precisely in the appropriate region. This invention proves such a new and useful system and method.

BRIEF DESCRIPTION OF THE FIGURES

FIG. 14 is a flowchart of a method of preferred embodiment.

DESCRIPTION OF THE EMBODIMENTS

The following description of the embodiments of the invention is not intended to limit the invention to these embodiments but rather to enable a person skilled in the art to make and use this invention.

1. Overview

Figure 1:
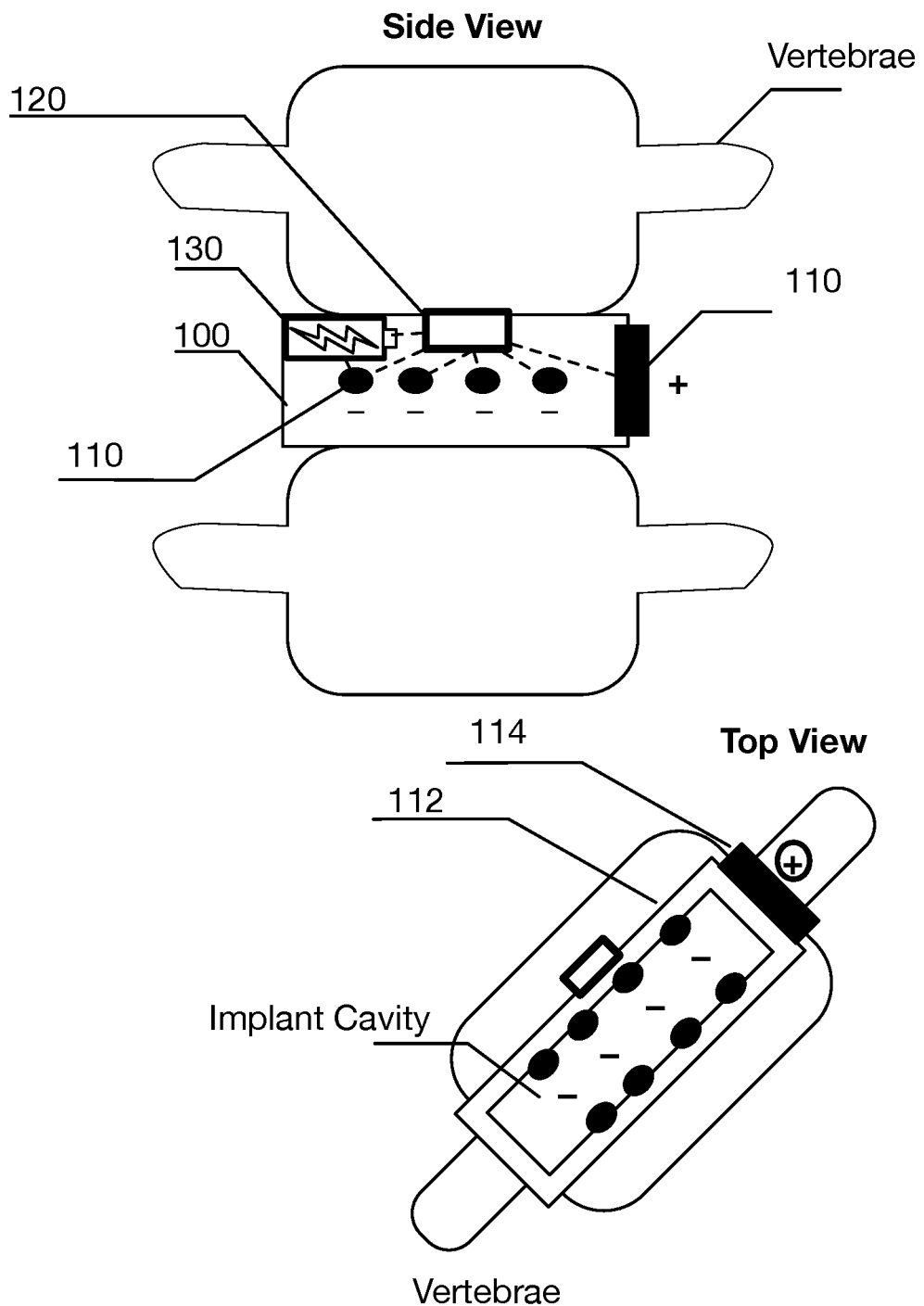
FIG. 1 is a schematic representation of a system of a preferred embodiment.

As shown in FIG. 1, a system and method to alter bone growth functions to allow more precise control of osteoinduction and osteolysis within specific spatial regions with respect to an implant with integrated electrical stimulation. More specifically the system and method may allow better control of electrically induced bone growth. By implementing at least one active electrode distal and/or isolated from a region of desired bone growth, more uniform bone growth may be induced in the desired bone growth region. Also, implementing one or more electropositive electrodes (anodes) external to the implant; controlled and potentially more uniform osteoinduction may be implemented within and around the implant body where bone growth is desired.

Additionally, undesirable effects of the anode(s) may be minimized by controlling the precise positioning and functionality of the anodes. This may be accomplished through multiple means. Cycling through multiple electrodes such that a single electrode functions as the anode only for short periods of time, may have a beneficial nonlinear minimization of the anode effects. Alternatively, positioning a single electrode as the anode may localize undesired effects to a single region, thereby having minimal negative effects from the system and method. The electrodes and the configured activation of those electrodes can be configured to promote a biased electric field during stimulation.

An alternative implementation, wherein the external electrode functions as an electronegative electrode (cathode), may allow for uniform osteolysis within the implant body. Herein, however, the system and method are primarily described in the formation for primarily promoting osteoinduction. The system and method may be applied to spinal fusion implants. However, the system and method may alternatively be used in other forms of orthopedic implants.

A potential benefit of the system and method is that with enhanced control of regions of electrical stimulation, bone growth dynamics may increase the likelihood of a successful spinal fusion. The system and method can be applied to an implant so that regions of osteoinduction and osteolysis are promoted in specific and targeted regions. In one example, the anode is positioned at a removed position on the external surface of an implant.

Another potential benefit comes with more uniform osteoinduction. Controlling and maintaining bone growth in a region may lead to greater bone mass densities, thus uniform osteoinduction may lead to the creation of more uniform and stronger bone structure, as opposed bone tissue created by a mix of osteoinduction and osteolysis.

Another potential benefit of the system and method is improved control of bone density and porosity. Increased control of osteoinduction may allow better control of bone formation, and the amount of bone formation, in a given region.

Another potential benefit is that preventing bone growth outside of the desired area of growth reduces the risk of bone growth onto soft tissue. Bone growth onto soft tissue may in fact damage the tissue and/or reduce the function of the tissue. Reducing the risk of damaging soft tissue thus helps minimize negative impacts of bone growth treatment.

The system and method may be implemented with any series of orthopedic implants, preferably in a region of bone growth. The orthopedic implant may itself contain electrodes such that the implant itself induces bone growth dynamics. The system and method may alternatively be implemented with other types of implants, wherein some other mechanism may be responsible for bone growth dynamics.

2. System

As shown in FIG. 1, a system for altering bone growth on or within an orthopedic implant includes: an implant body 100; a plurality of electrodes 110, that are at least partially embedded in the implant body; a control system 120, that controls the activity of each electrode from the plurality of electrodes; and a power system 130, that provides electrical power for the function of the plurality of electrodes. The system functions as an orthopedic implant that monitors and/or promotes bone growth. In some preferred variations, the system may additionally include a communication system enabling communication of implant components with external systems.

In some variations, the system may incorporate the system for altering bone growth on or within an orthopedic implant in an implant device such as the one described in U.S. patent application Ser. No. 15/075,152, filed 19 Mar. 2019, which is hereby incorporated in its entirety by this reference.

In preferred variations, the implant body 100 has an interior surface, defining an internal cavity; in addition to having an exterior surface.

The plurality of electrodes include: a set of primary electrodes 112, comprising at least one electrode, wherein a non-embedded segment of each primary electrode is proximal to a bone growth region that includes at least the defined internal cavity; and a set of secondary electrodes 114, comprising at least one electrode, wherein a non-embedded segment of each secondary electrode is distal to the bone growth region. Although in many preferred variations the bone growth region is a region of preferred bone growth, generally speaking, the bone growth region is a region for desired change in bone growth behavior (i.e. a region for induced bone growth or induced bone breakdown). The plurality of electrodes 110 are configured to function in a stimulation operating mode, wherein a subset of the primary electrodes 112 function to induce bone growth (or decay) and a subset of secondary electrodes 114 function in complement to the primary electrodes. In preferable variations, the subset of primary electrodes 112 function as cathodes, to induce bone growth, and the subset of secondary electrodes 114 function as anodes, to provide a current source. In other preferred variations a subset of primary electrodes 112 may additionally or alternatively function as anodes, to induce bone breakdown.

The control system 120 preferably includes a processor and circuitry that connects the control system to the plurality of electrodes 110. The processor, in some operating modes, can include machine instructions configured to control direction and magnitude of current traveling through each electrode from the plurality of electrodes.

The implant body 100 of a preferred embodiment functions as a structural element, housing or holding other implant subcomponents. The implant body 100 is preferably made of non-conductive material, but may be partially conductive. The implant body 100 may structurally serve a medical objective. The shape and form may be of those of other passive medical device implant body such as orthopedic implant devices like cervical plates, monoaxial screws, spinal cages, meshes, and pins. The implant body 100 is preferably integrated with the plurality of electrodes 100 such that electrical stimulation enhances recovery. The medical implant bodies may house some or all circuit elements (e.g., PCB, leads, antennas etc.) included as part of the implantable components. Preferably, the implant body 100 includes integrated electrode sites, which may be distributed across the geometry of the implant body. These integrated electrode sites may be distributed in such a way as to facilitate bone growth and bone reabsorption in distinct regions. In some embodiments, the implant body 100 can be a spinal implant, which may be a spinal cage. A non-exhaustive list of descriptions of typical spinal cages that may be incorporated with the system will follow. As spinal cages may be highly specialized for each individual implementation, all provided spinal cage specifications are provided as typical descriptions of that spinal cage and not presented as a limitation for each spinal cage per se.

The spinal cage variation of the implant body 100 may be made of a polymer, such as PEEK, or it may be made of engineered natural or synthetic bone material, or some other material. The spinal cage generally has an extruded prism geometry with many variations dependent on the specific type of spinal cage. As per a prism, the spinal cage geometry has an external surface comprising: a sufficiently, flat and opposing (e.g., parallel), top and bottom surface; and a more complex outer wall geometry that may be distinct to the specific spinal cage implementation. Herein opposing characterizes the general geometry of the top and bottom surfaces of the implant without requiring the surfaces to be parallel or flat and may include surfaces defined along intersecting planes. Preferably, the opposing surfaces are defined along planes with angular offset of 0-10 degrees though may be more. For example, in many implementations, the top and bottom surfaces are skew several degrees to achieve lordosis. As discussed here, the exterior perimeter of the spinal cage is defined as the perimeter along the lateral (i.e. side) wall geometry. The spinal cage can include one or more graft windows, which can be defined as internal implant cavities, wherein these internal implant cavities are defined by the interior surface of the spinal cage. Implant cavities are typically defined to be prism shaped with openings in the top and bottom of the spinal cage, which often functions to provide a through hole within which bone growth can occur. The interior surface of the spinal cage thus refers to the lateral walls that define the internal cavities. In some variations, internal cavities may have openings in addition to the top and bottom openings. As desired by implementation, these additional surfaces may also be included as part of the interior surface.

The spinal cage may be incorporated with many geometries including, but not limited to, anterior lumbar interbody fusion (ALIF) cages, transforaminal lumbar interbody fusion (TLIF) cages, posterior lumbar interbody fusion (PLIF) cages, anterior cervical fusion (ACF) cages, lateral cages and/or other suitable types of spinal cages. In some implementations the spinal cage geometry is an extruded prism of some defined form, which generally has a continuous outline and at least one defined internal cavity. More common geometries of the spinal cage may have a rectangular prism resemblance, and may be considered "sufficiently" rectangular to describe components with respect to the sufficiently rectangular implant body 100. The rectangular body comprises a top surface, bottom surface, two shorter sides, and two longer sides; an exterior surface comprising the lateral sides (i.e. the two shorter sides and the two longer sides); and an exterior perimeter that circumnavigating the lateral sides. In some variations the rectangular body may have some curvature and geometric features along some or all sides. This curvature may include curved edges of the implant body and/or curvature of the entire rectangular body. The spinal cage may include other design features such as: surface coatings, surgery tool attachment points, teeth, and/or other elements. The spinal cage is preferably composed of a non-conductive polymer, such as PEEK, but may be made of engineered, natural or synthetic bone material, titanium and/or other suitable material or combinations thereof.

Figure 3A:
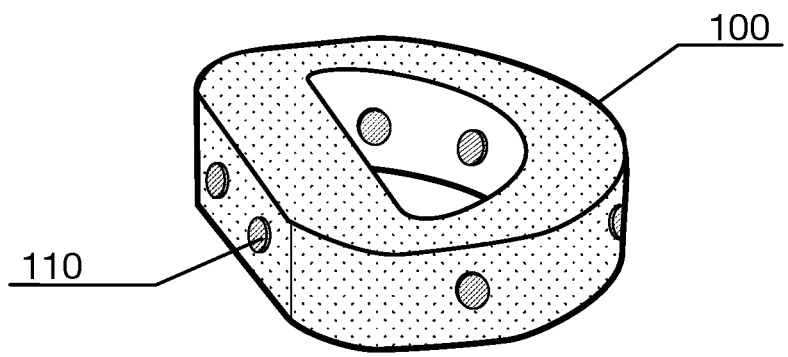
FIG. 3A is schematic representation of a perspective view of an ALIF cage of a preferred embodiment.
Figure 3B:
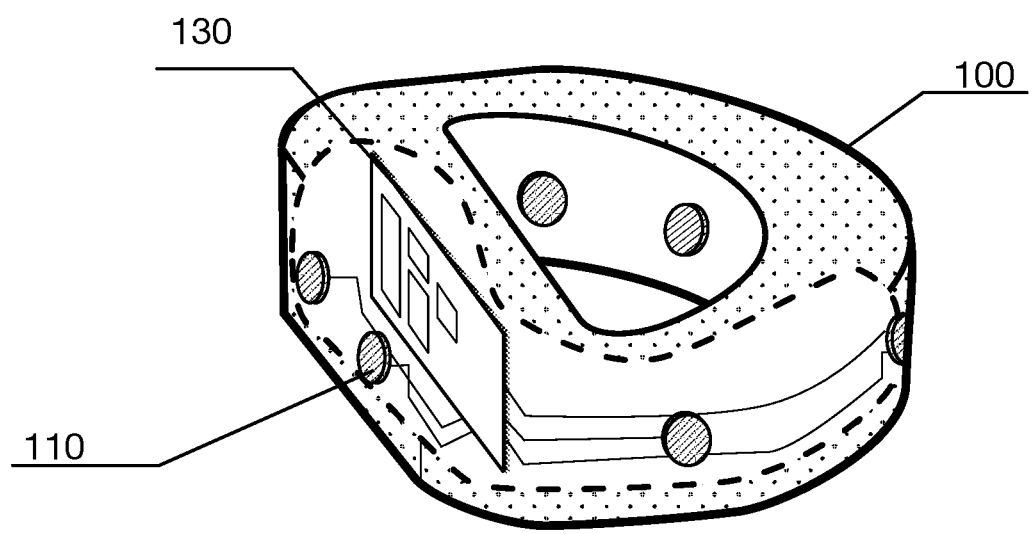
FIG. 3B is a schematic representation of a perspective view of an ALIF cage with an exposed window of internal components.
Figure 4:
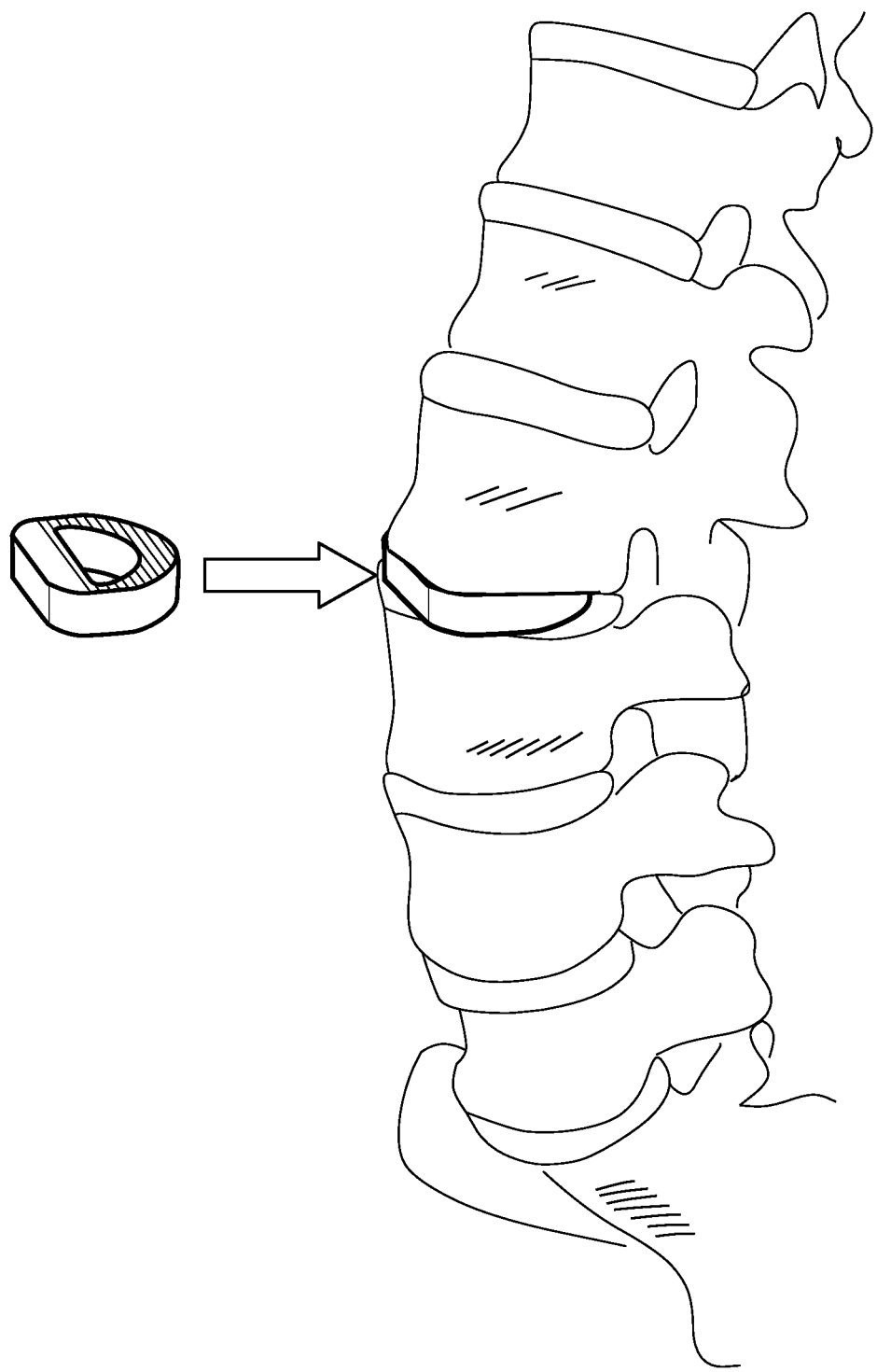
FIG. 4 is an illustration of an implantation of an ALIF cage of a preferred embodiment.

In some variations, the implant body 100 is an ALIF cage such as shown in FIGS. 3A and 3B The ALIF cage is typically optimized for implantation in the anterior lumbar region of the spinal cord for anterior lumbar interbody fusion as shown in FIG. 4. The ALIF cage is typically a larger spinal cage implant. Typical ALIF cages may vary between 10×25×35 mm-18×28×39 mm with an interior cavity space that may vary from 2.0 mL-8.0 mL.

Figure 6:
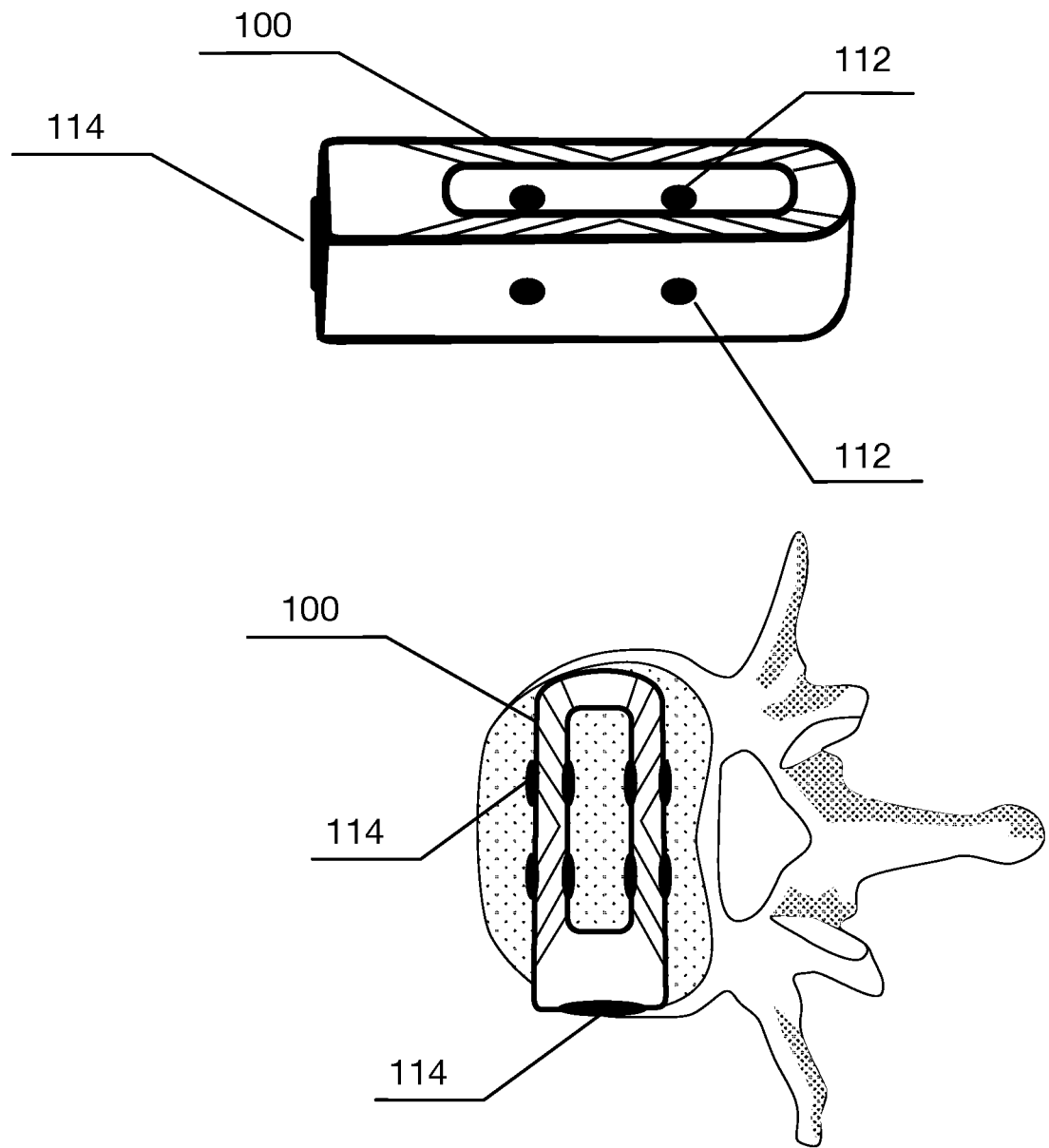
FIG. 6 is an illustration of a lateral cage implant body of a preferred embodiment.
Figure 7:
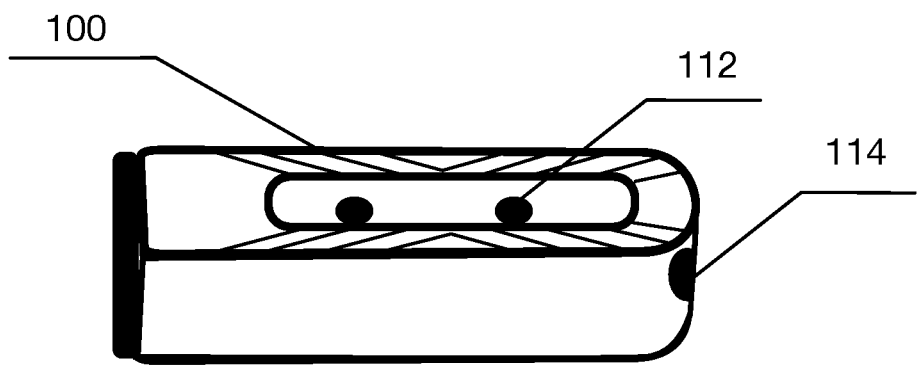
FIG. 7 is a second illustration of a lateral cage implant body of a preferred embodiment.
Figure 7:
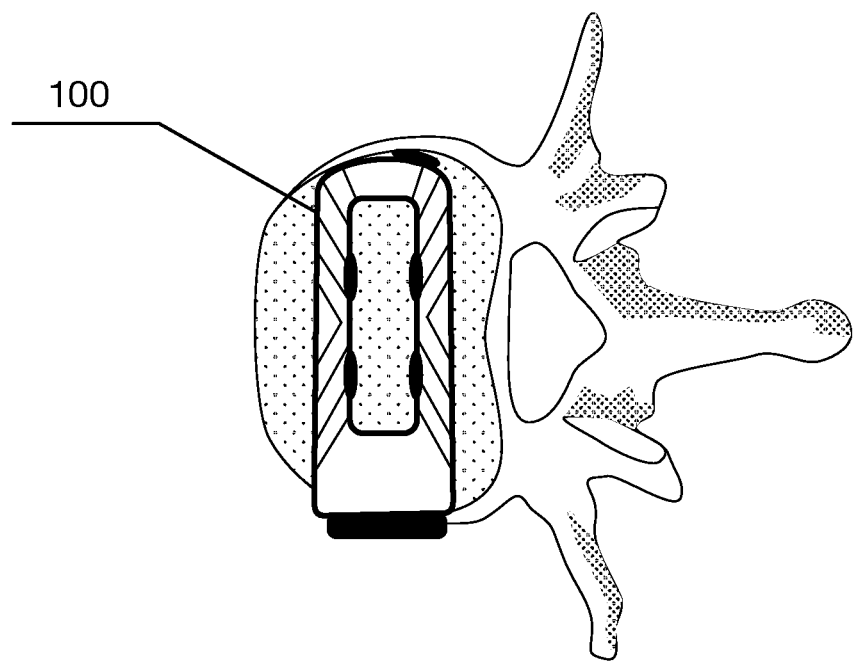
Figure 8:
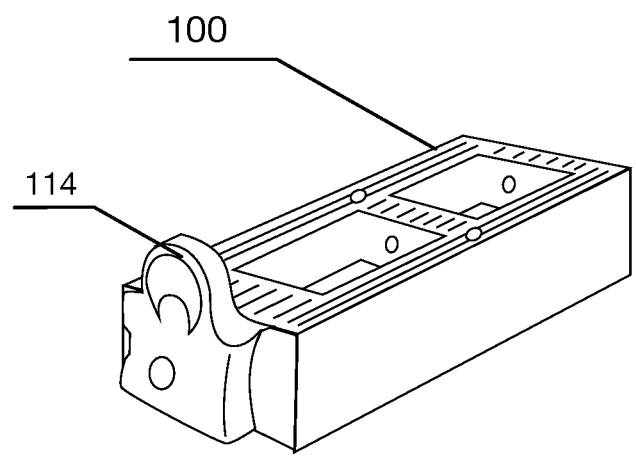
FIG. 8 is an illustration of a lateral cage implant body with external casing of a preferred embodiment.

In some variations, the implant body 100 is a lateral cage. FIGS. 6-8 show typical lateral cages. The lateral cage is typically more rectangularly shaped as compared to the ALIF cage and generally elongated along one dimension with two "end" surfaces being smaller in surface area than the adjacent "elongated" surfaces. Lateral cages may vary between 8×18×30 mm-14×21×60 mm, with an interior cavity space that may vary from 1.4 mL-11.6 mL.

Figure 9:
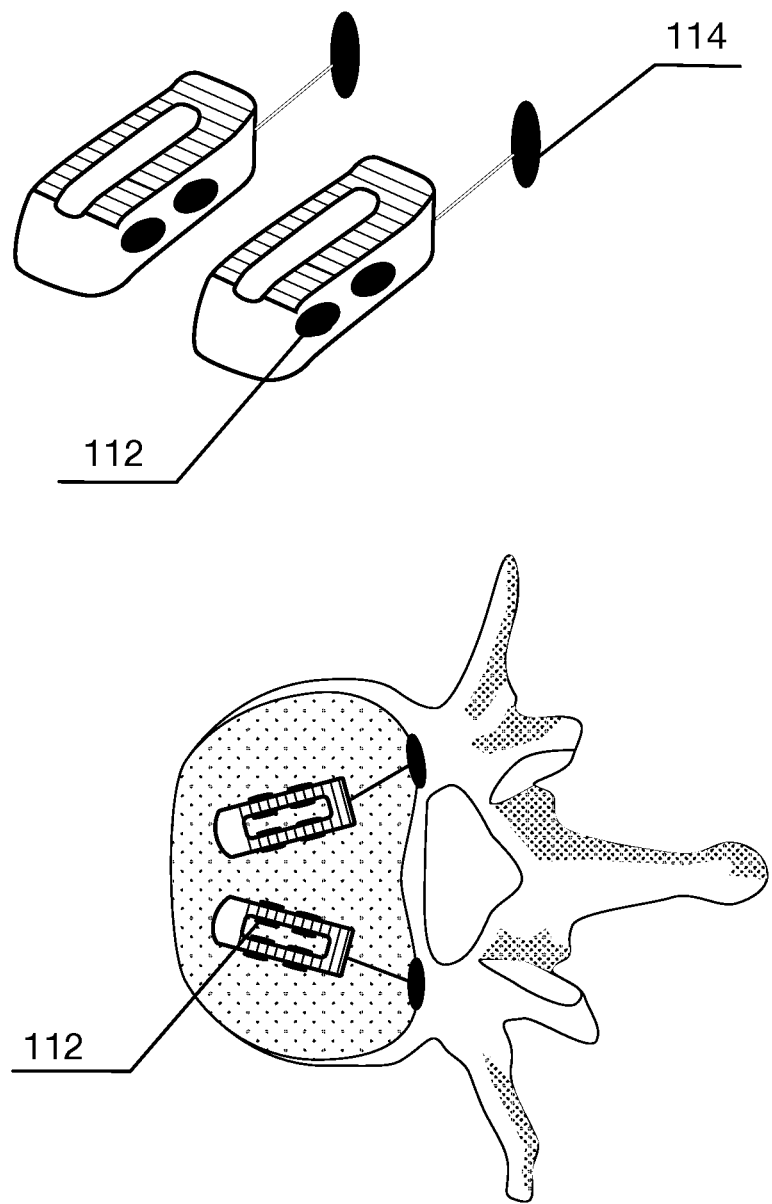
FIG. 9 is an illustration of a PLIF cage implant body of a preferred embodiment.

In some variations, the implant body 100 is a PLIF cage. FIG. 9 shows a typical PLIF cage. The PLIF cage may be a smaller implant body 100 as compared to the ALIF cage, preferably optimized for implantation in the posterior lumbar region of the spinal cord for posterior lumbar interbody fusion, wherein multiple implant bodies may be inserted between a pair of vertebrae. Typical dimensions of the PLIF cage may vary from 6×10×25 mm-16×12×32 mm.

Figure 10:
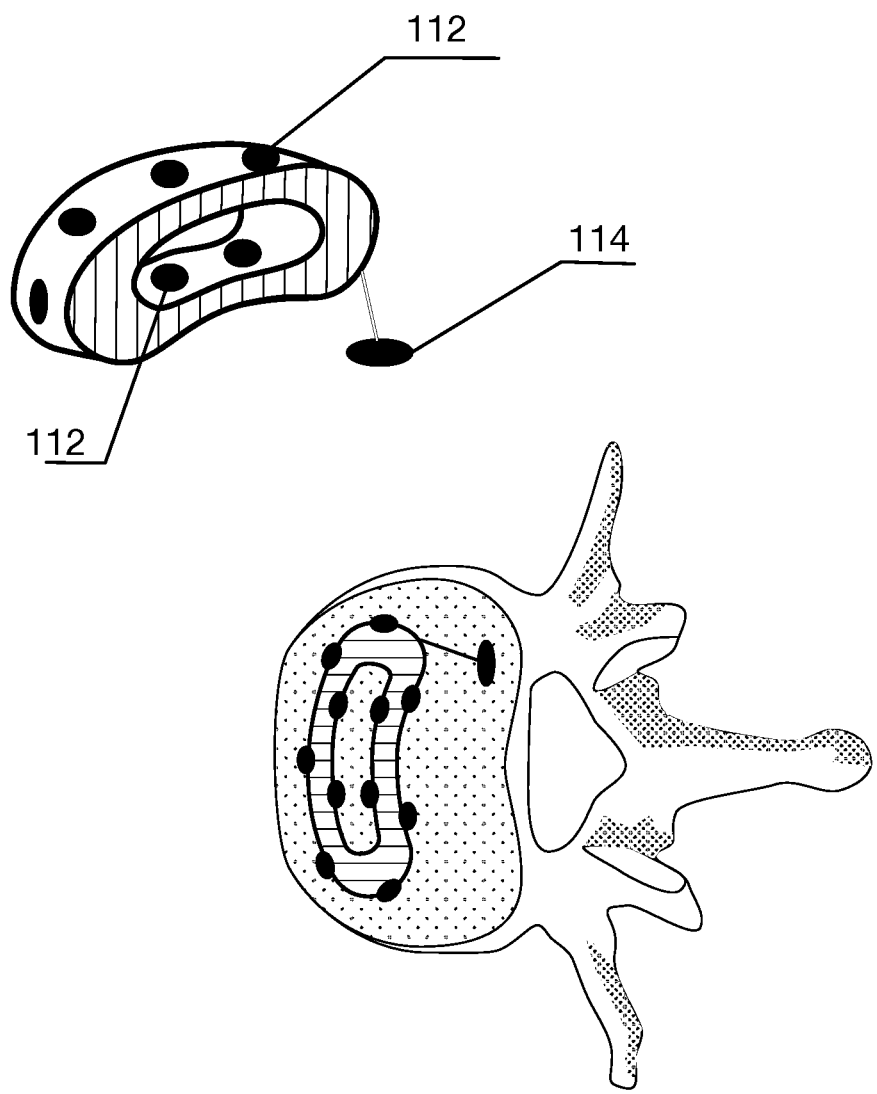
FIG. 10 is an illustration of a TLIF cage implant body of a preferred embodiment.

In some variations, the implant body 100 is a TLIF cage, such as shown in FIG. 10. The TLIF cage can be a more rectangular shaped spinal cage that may be used in small incisions for transforaminal lumbar interbody fusion, wherein multiple implants may be inserted between a pair of vertebrae. Typical dimensions of the TLIF cage may vary from 8×10×26 mm-16-11-34 mm. Additionally, the body of the TLIF cage may have a curvature.

In some variations, the implant body 100 is an ACF cage. The ACF cage may be a smaller square-like spinal cage implant inserted preferably between cervical vertebrae. Typical dimensions of the ACF cage may vary from 5×14× 11 mm-10×17×13, with an interior cavity space that may vary from 0.20 mL-0.9 mL.

In some variations, the implant body 100 may further include a metal casing, as seen in FIG. 1 and FIG. 8. In some implementations the metal casing may, in part, be conductively isolated from some or all of the plurality of the electrodes. The metal casing, or sub-portions of the metal casing, may additionally function as an electrode as described later.

In alternate variations the implant body may be an orthopedic implant that may or may not have an interior cavity. Orthopedic and non-orthopedic implants that may implement localized bone growth preferably include joint and extremity implants and other connective implants Examples of these implants include: hip implants, knee implants, implant plates, implant nails, and implant screws. The system may additionally be implemented with any other system implant wherein localized charge may be implemented to aid a patient.

The plurality of electrodes 110 of a preferred embodiment function to hold or transfer charge from and to the implant; and to and from the surrounding tissue. An electrode is preferably a conductive element that includes an electrode site (e.g., a conductive pad exposed to body tissue) connected (directly or indirectly) to other implant components (e.g., control system 120 and power system 130). The plurality of electrodes are preferably conductively isolated from the implant body 100 and exposed at a set of distinct electrode sites. The implant sites are preferably exposed electrode sites on or near the interior surface of the implant body 100 and/or on or near the exterior surface of the implant body 100. In some preferred variations, exposed electrode sites may include electrode sites distant from the implant body 100 (e.g., distant to desired bone growth regions). The electrode sites are distributed across the geometry of the implant body 100 in such a way as to facilitate the osteoinduction and osteolysis in desired bone growth regions during a controlled stimulation mode. The electrode site geometry can be configured for differing current density profiles.

In preferred variations electrodes are partially embedded in the implant body 100. These electrodes have at least one "embedded" region within the implant body 100 and at least one "exposed" region (i.e. exposed electrode site), such that the implant body 100 does not completely insulate the electric field generated by the exposed electrode site from external tissue. The exposed electrode site may be along an interior surface (e.g., exposed to an interior cavity or through hole) or an exterior surface (e.g., adjacent to external tissue) of the implant body 100. Embedded regions may include: regions where electrodes are molded into the implant body 100; run through slits and/or holes in the implant body; encased in regions of the implant body; and/or incorporated within the implant body in some other way. Embedded regions may vary significantly dependent on the size and/or shape of the electrode.

Each electrode may be of any desired shape and/or size. In some preferred variations, some electrodes may be wires exposed at defined electrode sites on and/or around the implant body 100. Other examples of electrodes may include, but are not limited to: thin wires, thick wires, layers of distinct wires, discs, metallic bodies, rings, covering shapes of the implant body 100, covering shapes of the implant body cavity, and/or any combination of the aforementioned examples. In one preferred variation the plurality of electrodes 110 include wires embedded and integrated within the implant body 100.

The exposed electrode sites of electrodes function to enable current transfer to tissue on, or near, the implant body 100. The electrode sites are preferably flush with the surface of the implant body 100 along the interior or exterior cavity of the implant body 100. Alternatively, the exposed electrode sites may protrude from the implant body 100 or be recessed within the implant body 100.

The electrodes of the plurality of electrodes 110 function to hold or transfer charge from and to the implant, to and from the surrounding tissue. Preferably at any given time, charge transfer occurs with a substantially equal charge, being generated at a source and dissipated at a sink; thereby creating an electric field that may induce bone growth, osteoinduction; or bone breakdown, osteolysis. The electrodes are preferably configured for electrical stimulation at, within, and/or around the implant body 100. Electrodes of the system may further be characterized as any material that may function as a cathode or anode of a circuit, allowing current to flow from one to the other.

Electrodes preferably function as anodes and cathodes, i.e. current sources and current sinks respectively; to create regions of bone growth, osteoinduction, and bone breakdown, osteolysis. Thus, the plurality of electrodes 110 are preferably situated such that, at least one electrode has an exposed electrode site in a "bone growth" region, to induce osteoinduction or osteolysis. A bone growth region generally characterizes one or more regions relative to an implant body. As desired, the system may have multiple bone growth regions. Dependent on implementation, circumstances regarding the current status of bone growth, and potentially other factors, the desired activity in the bone growth region may change over time. Thus, a specific bone growth region may at times be a region for osteoinduction, osteolysis, or no activity. In other words different bone growth regions may be defined for active bone growth, bone deterioration, or no or minimal changes to bone structures. In preferred variations, wherein the implant body 100 contains an internal cavity, the internal cavity is preferably a bone growth region. In alternate variations, the internal cavity is not a bone growth region.

Each electrode from the plurality of electrodes 110 is preferably enabled for independent function. Alternatively, sets of electrodes are enabled to function independently as a set. Independent function enables precise control of current through each electrode such that the direction and magnitude of current through each electrode, or each set of electrodes, may be individually determined and set, as desired. Additionally in some preferred variations, the type of current can also be independently controlled (e.g., direct current or alternating current).

In some alternate variations, electrode function has limited and/or fixed operation. For example, the system may have a "fixed" source, wherein one set of electrodes may only function as a current source, while another set of electrodes may function only as a current sink.

The plurality of electrodes 110 preferably includes at least one electrode proximal to the bone growth region, i.e. a set of primary electrodes 112. Primary electrodes 112 function to induce osteoinduction and/or osteolysis in the bone growth region as desired. In a configuration for primarily promoting osteoinduction, primary electrodes 112 are configured to typically function as cathodes (current sinks). The set of primary electrodes 112 is preferably proximal to the bone growth region and may be positioned inside, on, or around the desired region of bone growth. In preferred variations, wherein the implant body 100 contains integrated electrode sites, a subset of primary electrodes 112 may be located on or within the integrated electrode sites of the implant body 100. Primary electrodes 112 may have any desired size or shape as generally described for electrodes (e.g., thin, thick, straight wire, spiral wire, ring, disc, covering shape, etc.).

The plurality of electrodes 110 may further include at least one electrode distal to the bone growth region, i.e. a set of secondary electrodes 114. In some variations, the set of secondary electrodes may additionally be distal to the implant body 100. In other variations, the set of secondary electrodes 114 may be attached and exterior to the implant body 100 (e.g., the metal casing implemented as a secondary electrode). The set of secondary electrodes 114 may function as a charge counterbalance to the charge generated by primary electrodes 112. For example, if the set of primary electrodes 112 generate a net negative charge to induce osteoinduction, the set of secondary electrodes 114 may generate a net positive charge to balance the primary electrodes and act as a current "source" to the primary electrode "sink". Accordingly, if, for example, 1 μA of current is sinked by one set of electrodes constituting a plurality of electrodes utilized in a system, then 1 μA of current simultaneously needs to be sourced by the remaining electrodes constituting a plurality of electrodes utilized in that system (conservation of charge). In some preferable variations, the surface area of the set of secondary electrode 114 is of similar size as compared to the surface area of the set of primary electrodes 112. Alternatively, the surface area of the set of secondary electrodes may be smaller or larger than the surface area of the set of primary electrodes 112.

As secondary electrodes 114 are positioned distal to the bone growth region, there is some flexibility in how they may be implemented in the system. In some variations, secondary electrodes 114 comprise a single (possibly larger) electrode with an exposed region far from the implant body 100. This secondary electrode 114 may have a region embedded in the implant body 100, but may alternatively not have an embedded region. In a second variation, the system may comprise multiple secondary electrodes 114 along the exterior of the implant body 100. This may particularly be the case for larger implants wherein the bone growth region resides only in the internal cavity of the implant body 100. In a third variation, wherein the system has multiple bone growth regions, that may additionally vary over time; the system may include a set of secondary electrodes 114 wherein only a subset of the secondary electrodes actively function as secondary electrodes at any one given time. For example, where secondary electrodes 114 are along the exterior surface of the implant body 100, exposed to healthy bone tissue; the active set of secondary electrodes 114 (i.e., subset of secondary electrodes) may vary (e.g., cycle around the implant body) over time such that osteolysis is not induced in the healthy bone tissue.

It should be noted that the designation of primary electrodes 112 and secondary electrodes 114 describes a relative proximity of electrodes to a bone growth region, and thus their most likely intended utilization. Generally speaking, primary electrodes 112 and secondary electrodes 114 may have the same functional capabilities; although these capabilities may be limited by the size, shape, material construction, and location of the electrode. A subset of primary electrodes 112 may function as cathodes while another subset of primary electrodes may function as passive (neither sourcing nor sinking current), and another subset of primary electrodes may function as anodes (e.g., to induce osteolysis), wherein any of the subsets of primary electrodes may contain, all, some, or no electrodes. Similarly, a subset of secondary electrodes 114 may function as cathodes, while another subset of secondary electrodes may function as passive, and another subset of secondary electrodes may function as anodes. Any subset of secondary electrodes 114 may contain zero, some, or all secondary electrodes. As mentioned previously, secondary electrodes 114 may contain a polarity to counter-balance the primary electrodes 112. Alternatively, the set of secondary electrodes 114 may have another polarity (or no polarity) for other functions. Alternatively, the set of secondary electrodes 114 may counter-balance the set of primary electrodes 112 (or a subset of primary electrodes) to a greater or lesser degree (e.g., a time average). In preferred variations, the functionality of electrodes in each set of primary and secondary electrodes may be changed dynamically as seen necessary. Alternatively, the functionality of electrodes in each set of primary electrodes 112 and/or set of secondary electrodes is 114 fixed, or a subset of primary and/or secondary electrodes have a fixed functionality.

In some preferred variations, the region of desired bone growth is the implant body 100. In one implementation, the entire set of primary electrodes 112 function primarily as cathodes and the entire set of secondary electrodes 114 function as anodes that counter-balance the primary electrodes. This example may induce osteoinduction in proximity to the primary electrodes, and/or inhibit (or reduce) osteolytic activity within proximity of the primary electrodes, and promote osteolysis in proximity to the secondary electrodes. In one implementation of this example, the set of secondary electrodes 114 comprises a single electrode that is the metal casing outside of the implant body 100, as shown in FIG. 1. Alternative implementations of the secondary electrode in the above example may include, but are not limited to, the set of secondary electrodes being a ring outside of the implant body or the set of secondary electrodes being two electrode bodies at opposite poles of the implant body 100. The set of secondary electrodes 114 may, additionally or alternatively be any shape, and/or size, desired.

Figure 11:
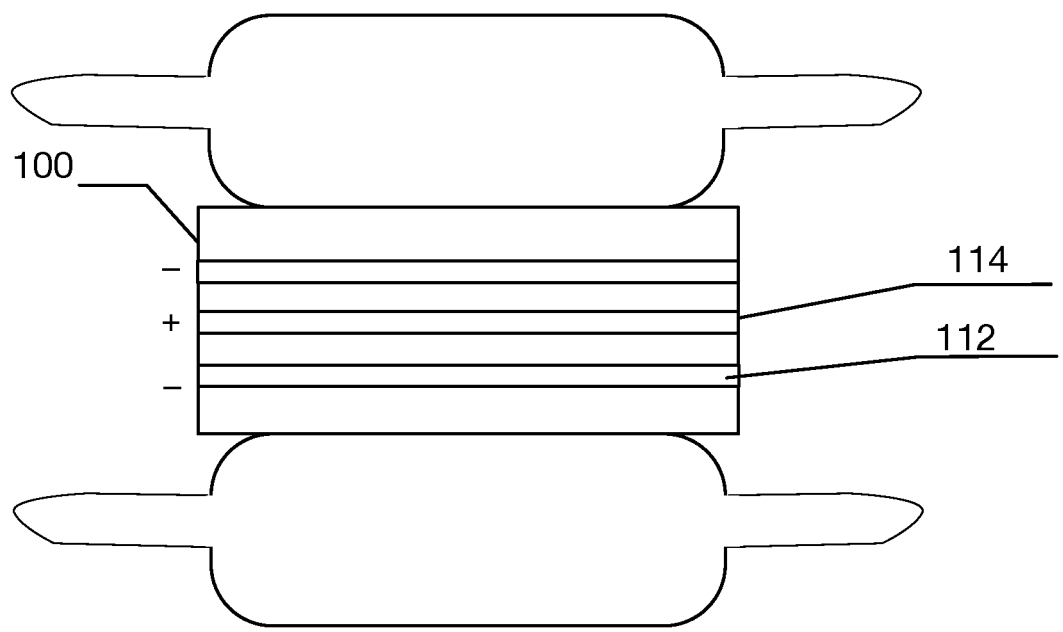
FIG. 11 is an alternate schematic representation of a system of preferred embodiment.

In another preferred example, as shown in FIG. 11, primary electrodes 112 are incorporated as rings (or other preferred shapes) on the upper and lower regions of the implant body 100 internal cavity, while a secondary electrode 114 ring is implemented in between the two primary electrodes rings. The secondary electrode 114 ring may function as an anode, while the primary electrode 112 rings are cathodes to induce osteoinduction directly above and below themselves to ensure osteoinduction in the endplate regions (e.g., to help fuse the implant body with the vertebrae directly above and below the implant body) In other preferred examples, the primary electrodes 112 and secondary electrodes 114 may be moved closer or further apart to change the size and location of the bone growth region and to alter the containment of osteolysis. Additionally or alternatively, polarity of the electrodes may be changed or turned off as deemed fit for bone growth. In a related approach, the secondary electrode 114 could be configured as an anode and be a large surface plate and a set of primary electrodes 112 could be configured as cathodes and can be positioned so as to circumscribe the secondary electrode so as to contain the region of osteolysis.

Each electrode from the plurality of electrodes 110 may additionally be made of different materials. Electrodes are preferably made of metallic compounds and/or other type(s) of material that readily conduct electricity and are biologically non-toxic. Examples of electrode material may include, but are not limited to, platinum (Pt), titanium (Ti), iridium (Ir), oxidized iridium, and titanium nitride. Alternating current (AC) or direct current (DC) impedance of different electrode materials may be significantly different. Using different materials for distinct electrodes, functioning as the electro-negative electrode and/or the electro-positive electrode, may allow using larger (or smaller) electrical potentials to pass net faradic or non-faradic current through an electrode. For example, for electrodes of a given surface area, the DC impedance of a cathode/anode pair constructed using titanium will be higher than that of a pair constructed using platinum, for electrode sizes and currents appropriate for electrical stimulation of bone. In addition, the DC impedance of titanium anodes may further increase due to the metal readily oxidizing which is less of a concern for platinum electrodes. More generally, the externally generated potential (electrical potential supplied actively using a circuit) that needs to be applied between electrodes when using different materials to drive a desired current varies greatly depending on: the content and concentration of ions in the fluid that the electrodes are in contact with, the materials themselves, material of the anode, material of the cathode, and/or other suitable factors. As such, for some electrode material choices, very little or no potential may be required to pass current between the anode and the cathode.

Since power is the product of current and electrical potential ($P=V*I$), the choice of materials making up the anodes and cathodes may greatly impact the amount of power that needs to be supplied by the power system in order to cause osteoinduction/osteolysis. This is of special concern in implantable systems where power required to drive current between the electrodes is provided wirelessly since it is difficult to transmit large powers over large distances. Power requirements can impact at what depth a system can be implanted where a system that utilizes anode/cathode materials. For example, a system with anode/cathode materials where small potentials are applied over the cathodes/anodes to drive a desired current may be implanted deeper into a patient compared to a system that utilizes anode/cathode materials where larger potentials are preferably used to drive the same current since the latter requires more power. A greater power consumption also requires larger power sources, which may affect the bulk of the implant and/or power system.

Additionally, certain types of electrode materials may allow for distinct types of bone growth dynamics. In one example, osteoinduction may occur at both the cathode and the anode electrodes where both the cathode and the anode electrodes are constructed from platinum. In an alternate example, where cathode electrodes are constructed of platinum and anode electrodes are constructed of titanium, osteoinduction may occur in proximity of the cathode electrodes, while osteolysis may occur in proximity of the anode electrodes.

The plurality of electrodes 110 may comprise of distinct subsets of electrodes. Wherein a first subset of electrodes is constructed with a first material and at least a second subset of electrodes is constructed of a second material. The first material is preferably different from the second material. In some variations, additional subsets of electrodes made of distinct materials may be used. In one example, comprising of two subsets of electrodes, a first subset of electrodes may be constructed from titanium while a second subset of electrodes may be constructed from platinum.

Figure 12:
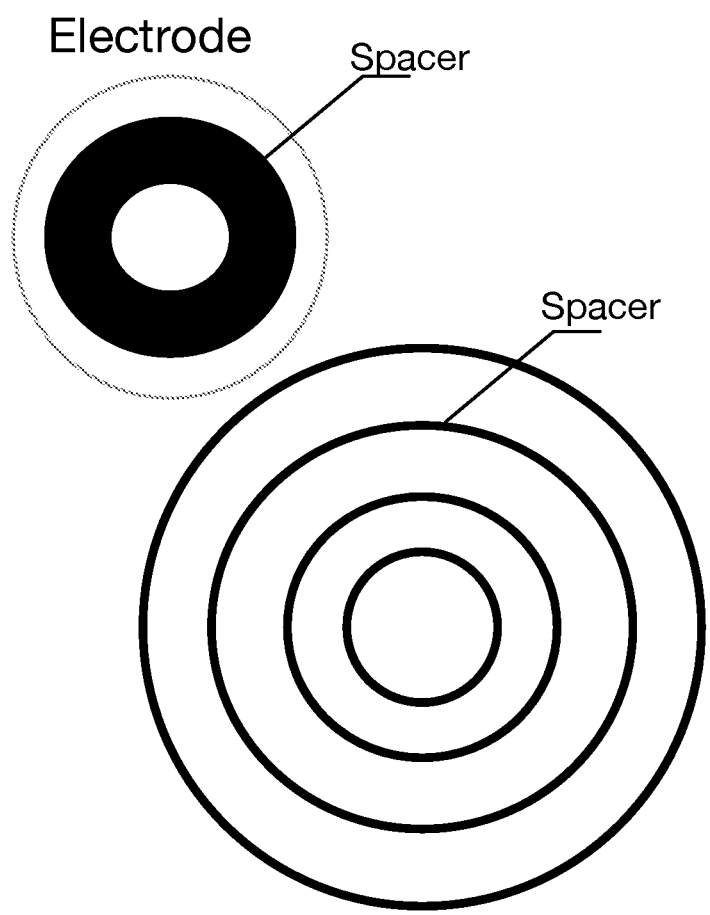
FIG. 12 is an schematic representation of an multi-component electrode of a preferred embodiment.

Additionally, electrodes may be composed of multiple distinct materials. An electrode may have multiple electrode sub-regions within an electrode site. The electrode sub-regions can be made of different material compositions. For example, in one implementation a subset of electrodes may have platinum on the exterior, an insulating spacer, and a titanium on the interior, as shown in the first diagram of FIG. 12. Alternatively titanium may be on the exterior and platinum on the interior, with or without the spacer. Electrodes may additionally be constructed of multiple layers in the same fashion, as shown in the second diagram of FIG. 12. Electrodes may alternatively be constructed of multiple distinct materials organized differently as compared to FIG. 12. For example, an electrode may be made of distinct materials that are lined adjacent to each other or coiled about each other.

Figure 13:
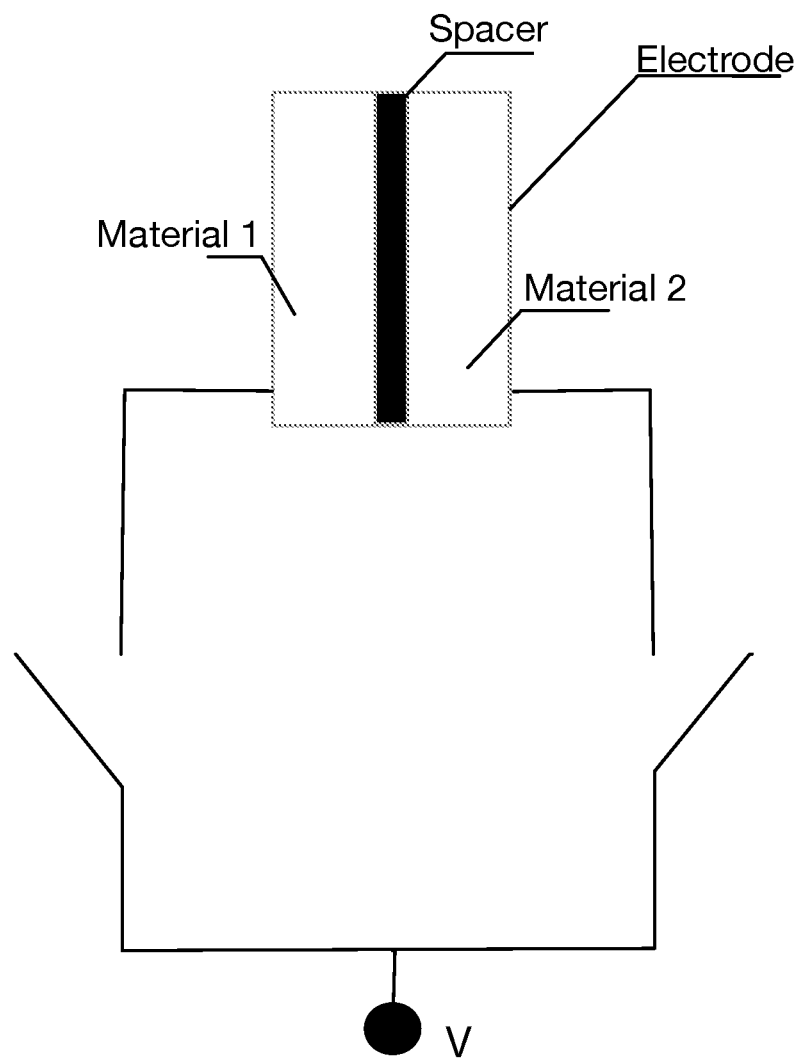
FIG. 13 is an alternate schematic representation of a multi-component electrode of a preferred embodiment.

Electrodes constructed of multiple types of materials may allow for dynamic operating modes, wherein the electrode may switch operation from one material to another material. That is, a single electrode may switch from one material functionality to another material functionality as deemed fit. For example an electrode comprised of a platinum and titanium layer, may activate the titanium active mode and thus the titanium layer of the electrode may pass current while the platinum layer stays uncharged. Alternatively the platinum layer may pass current while the titanium layer stays inactive. Alternatively, both layers may become active or inactive concurrently. A control system can preferably dynamically control the mode of activation of electrodes with multiple electrical stimulation modes. For example, a single electrode side may be able to use a digitally controlled switch to selectively activate different material constructions as shown in FIG. 13.

Electrodes constructed of multiple types of material may additionally have a dual operating mode (multi-operating modes), wherein distinct layers of the electrode simultaneously function in a distinct manner. That is, a singly positioned electrode site may have distinct sections (e.g., a platinum and a titanium section) where one section functions as an electro-negative electrode and another section functions as an electro-positive electrode. In one implementation where potentially precise and localized bone growth is required, dual operating mode electrodes may have an electro-negative exterior and an electro positive interior creating a short range electric field between the two layers allowing for precisely controlled osteoinduction and/or osteolysis.

The arrangement, shape, form and/or other physical properties of the primary electrodes 112 and/or the secondary electrodes can preferably 114 be set into a configuration for biased stimulation in and around the implant. Here, biased implies that tissue in and around the implant would receive proportionally more charge as compared to unbiased regions. Additionally, through different operation modes, these biased regions of functionality may be changed over time; both to balance negative or positive effects of stimulation, and to take into account for changes in local tissue development (e.g., bone growth).

The control system 120 of a preferred embodiment may function to control the charge amplitude and polarity of the plurality of electrodes 110. The control system preferably includes a processor and circuitry to connect to the plurality of electrodes 110. The control system 120 may additionally control, sync, and/or operate other components as deemed necessary. In some preferred implementations, wherein electrodes have multiple functionalities (e.g., dual activity circuit electrodes), the control system preferably controls and changes these functionalities. The control system 120 preferably controls the dynamic and multi-operating modes of the electrodes, either as distinct electrodes or as subsets of electrodes. The control system 120 may be implanted, as part of the implant body 100 or as a distinct system entity; may be located outside of the body; or may include a combination of implantable and non-implantable components.

The control system 120 preferably includes a processor allowing it to control each individual electrode distinctly, and/or subsets of electrodes as one group. The control system 120 may function autonomously, but may additionally, or alternatively, be controlled by a user through an external remote control device or communication system. In one implementation, where the implant body 100 is non-conductive, the control system 120 may allow current to be only applied at the surface of the electrode sites, thus allowing the distribution of current density to be controlled by the placement of the electrodes as well as their state during stimulation. Alternatively, the electrodes can be conductively isolated from a subset of the other electrodes and more preferably conductively isolated from each of the set of electrodes such that each electrode could be independently controlled such that current density may be similarly controlled by the control system 140.

The control system 120 preferably includes circuitry effectively connecting the control system with other system components. In preferred variations this includes the plurality of electrodes 110. Additionally, the circuitry may connect to the implant body 110, power system 130, or any other desired component. Circuitry may be "wired" or wireless.

The system preferably has multiple operating modes wherein the control system 130 is configured to activate the plurality of electrodes 110 to function in specific ways. Preferably, the system includes at least a stimulation operating mode, and a monitoring operating mode. In some preferred variations, the system may include a switching operating mode. The system may additionally include other operating modes (e.g., a calibration operating mode). Operating modes may function simultaneously, or distinctly, within the entire system and/or within each system subcomponent. For example, in one preferred implementation, the control system 130 may activate a subset of the plurality of electrodes 110 to operate in a stimulation mode, and activate another subset of electrodes to function in a monitoring mode.

The system is preferably configured to operate in a stimulation mode. In a stimulation mode, control system 120 is configured to activate a subset of the plurality of electrodes 110 to send current through tissue to induce either osteoinduction or osteolysis in the tissue as desired. Depending on how the system is implemented, the stimulation mode may enable different types of functionalities.

In one example of a stimulation operation mode, the control system 120 activates a subset of primary electrodes 112 to function as a sink, to induce osteoinduction in a bone growth region; and activates a subset of secondary electrodes 114 to as the current source.

In a similar example, the activity of the primary electrodes 112 is not changed, but the control system 120 changes the subset of secondary electrodes 114 electrodes designated as the current source (e.g., so as not to induce significant amounts of osteolysis in surrounding tissue). In one implementation, wherein the secondary electrodes 114 are positioned at exposed sites along the exterior surface of the implant body 100; the control system 120 may cycle through active subsets of secondary electrodes, such that, over time, the activated subset of active electrodes circumnavigates the implant body 100. This type of switching behavior may enable the changing of the position of the active secondary electrode(s) 114. In some cases, there may be no one ideal location for the secondary electrode and so changing position may promote more desired bone growth. For example, an anode may typically induce osteolytic effects in bone tissue, but a transient cyclical anode may ameliorate this effect.

In a third example, wherein both osteoinduction and osteolysis is desired, the control system 120 may activate a subset of primary electrodes 112 to function as current sinks in one bone growth region to induce osteoinduction, and activate another subset of primary electrodes to function as current sources in another bone growth region to induce osteolysis; and activate a subset of secondary electrodes 114 to balance the current as required. In one implementation of this example, the two bone growth regions are completed isolated, such that the control system may activate two subsets of secondary electrodes 114 to counter balance both subsets of primary electrodes 112. In another implementation, the two subsets of primary electrodes 112 are connected and the subset of secondary electrodes 114 counterbalances the net charge of both subsets of primary electrodes 112.

In a fourth example, wherein the plurality of electrodes 110 include electrodes composed of both titanium and platinum; the control system 120 may activate a subset of electrodes to induce bone growth, wherein the platinum section of the electrode functions as a current sink and the titanium section of the electrode functions as a current source.

In a fifth example, wherein a primary electrode 112 is a circuit composed of two materials along parallel circuits with a switch; the control system may switch between the activity of the material. The control system may initially activate the platinum wire to function as a cathode to induce osteoinduction, but later switch to the titanium wire and activate the titanium wire to function as an anode to induce osteoinduction.

In preferred variations, the system also includes a monitoring mode. In the monitoring mode, the control system 120 is configured to utilize electrodes to determine tissue composition. In the monitoring mode, the control system may activate and current through pairs of electrodes thereby measuring the impedance in the tissue between the pair of electrodes.

In this manner, the monitoring mode may be used to monitor the bone growth within the bone growth region. Preferably, monitoring bone growth involves the control system 120 driving AC signals between pairs of electrode and thus through the intermediary tissue. By measuring the impedance, through the tissue, the relative tissue composition (i.e. amount of bone growth) may be determined. By using this measurement between electrode pairs located on the outside perimeter of each bone growth region, the control system 120 may generate an impedance profile of the entire region. In the application of spinal fusion, the impedance profile can be used to monitor the degree of bone growth, and thus spinal fusion achieved. In preferred variations, the monitoring mode is used to measure and monitor bone growth. The monitoring mode may be used in conjunction with the stimulation mode to monitor bone growth activity and then alter the bone growth activity as desired; either automatically or after physician approval.

To facilitate high level monitoring through impedance measurements, the implant may include implant bone growth monitoring circuitry which functions to measure bone growth through impedance measurements of through the monitoring mode. Bone monitoring in this manner may be beneficial in reducing dependence on more complicated, slow, and expensive monitoring techniques such as MRI, ultrasound or x-rays conducted at a healthcare facility. The optional implant bone growth monitoring circuitry can be used to measure the impedance of the tissue between pairs of one or more electrodes.

The power system 130 of a controlled embodiment functions to give power to charge the plurality of electrodes 110. The power system 130 preferably includes a power source and circuitry to transmit the power to the plurality of electrodes 110. The power system 130 may further power any additional components that require power. The power system may comprise of any general power source, or a multitude of power sources (e.g., electrical outlet, internal generator), but may comprise of a battery (or several batteries). The power system may alternatively, be powered through wireless power coupling or other suitable forms of remote power delivery. The power system may be implanted, as part of the implant body 100 or as a distinct system entity; may be located outside of the body; or may include a combination of implantable and non-implantable components. The power system may be connected to each electrode through wiring, or may alternatively charge electrodes through induction or other means. In some variations the power system may comprise of an external electrical source. External wiring may then be used to connect the power source to the implant body 100. Alternatively, the power system may have a transmitter placed on, or near, the patient's body that can induce power into the implant body 100 and electrodes.

In some variations, the system may additionally include a communication system. The communication system functions to allow communication between internal implanted components and external components. The communication system may allow giving input to the electrodes through the control system 140. The communication system may additionally or alternatively allow for additional exchanges of command and/or data. For example, the communication system may send information about the generated fields from the electrodes to an external source. The communication system may be a hardwired system that physically connects external and internal components, but will preferably be a wireless system. The wireless system may function over resonant inductive coupling, RF irradiation, IR ultrasound or any other wireless medium.

The following section provides sample preferred implementations of the system with the commonly used spinal cage implants described previously. As these examples are in no way exhaustive, examples described for one implant body 100 may be combined or exchanged with another implant body implementation as desired.

Figure 5:
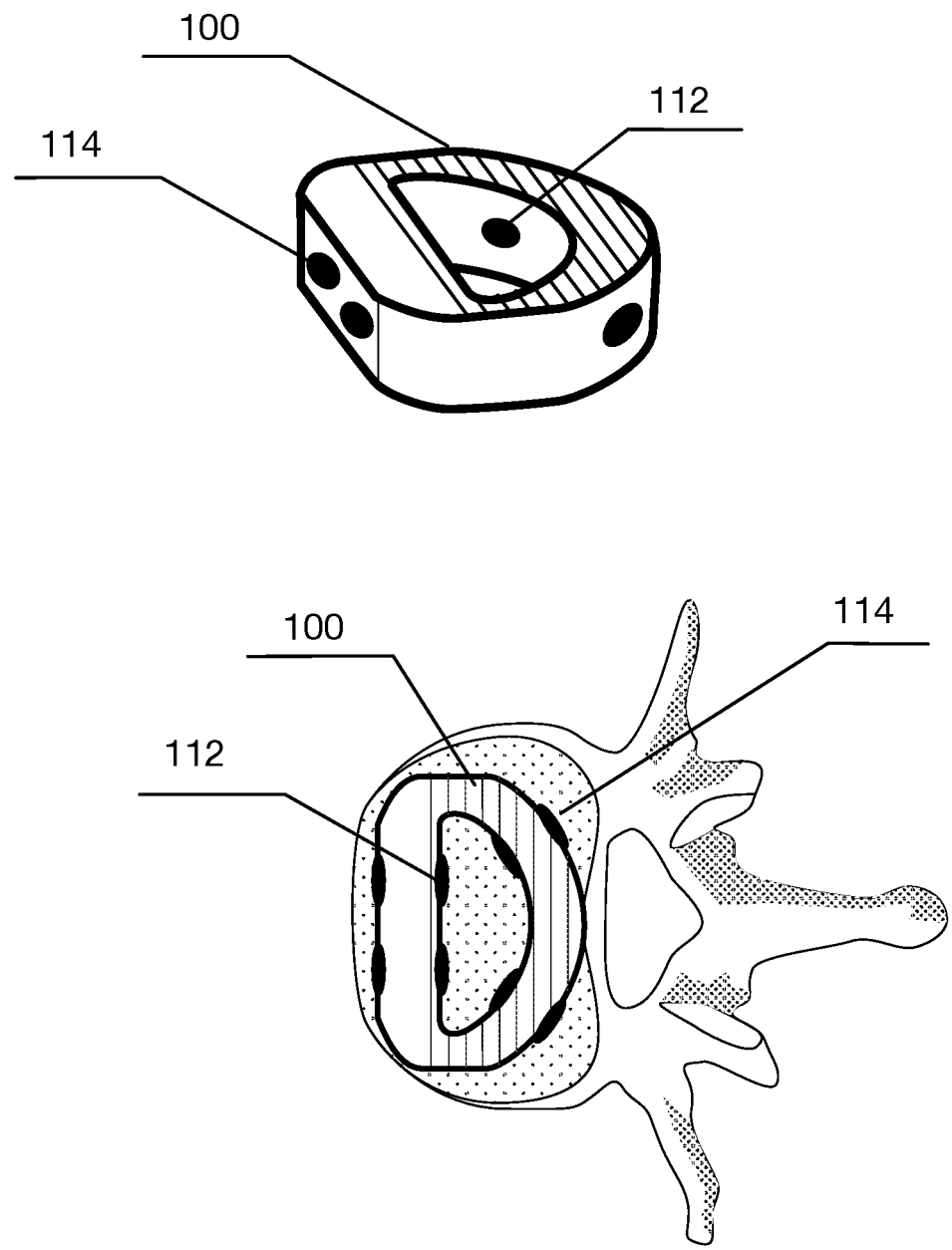
FIG. 5 is an illustration of an ALIF cage implant body of a preferred embodiment.

As show in FIG. 5, the ALIF cage is a spinal cage that may be implanted from the anterior side. As a "larger" implant, the ALIF cage preferably has only a bone growth region in the internal cavity of the implant body 100. For this variation, the primary electrodes 112 may be along the interior surface of the ALIF implant body 100, while secondary electrodes 114 are along the exterior perimeter of the implant body 110. In one preferred example, primary electrodes 112 include four electrodes exposed along the internal cavity (e.g., two electrodes along the posterior interior surface and two electrodes along the anterior interior cavity surface; and secondary electrodes 114 include four electrodes along exposed on the exterior surface (e.g., two electrodes on the anterior surface and two electrodes on the posterior surface of the implant body 100).

In an alternative variation, the ALIF cage may additionally include a bone growth region on the anterior side of the implant body 100. In this variation, primary electrodes 112 may additionally be along the anterior exterior surface of the implant body 100, while secondary electrodes 114 may then just be along the posterior exterior surface of the implant body 100.

In some implementations, the bone growth region may be a narrower region of the interior cavity (e.g., the bone growth region includes regions close to the upper and lower vertebrae). FIG. 11 shows this implementation. In these implementations, the primary electrodes 112 may include a ring along the interior cavity close to the top surface of the implant body 100 and a ring along the bottom surface of the interior cavity close to the adjacent lower vertebrae. Secondary electrodes 114 may comprise an internal ring as shown in FIG. 11, or may alternatively comprise of electrodes exterior to the implant body 100 as described in other variations.

In some variations the secondary electrodes 114 external to the spinal region (anterior side) may comprise a metal casing, or conductive attachment extending from the spinal cord region. In one example, the only a portion of the metal casing is the secondary electrode 114.

Figure 2:
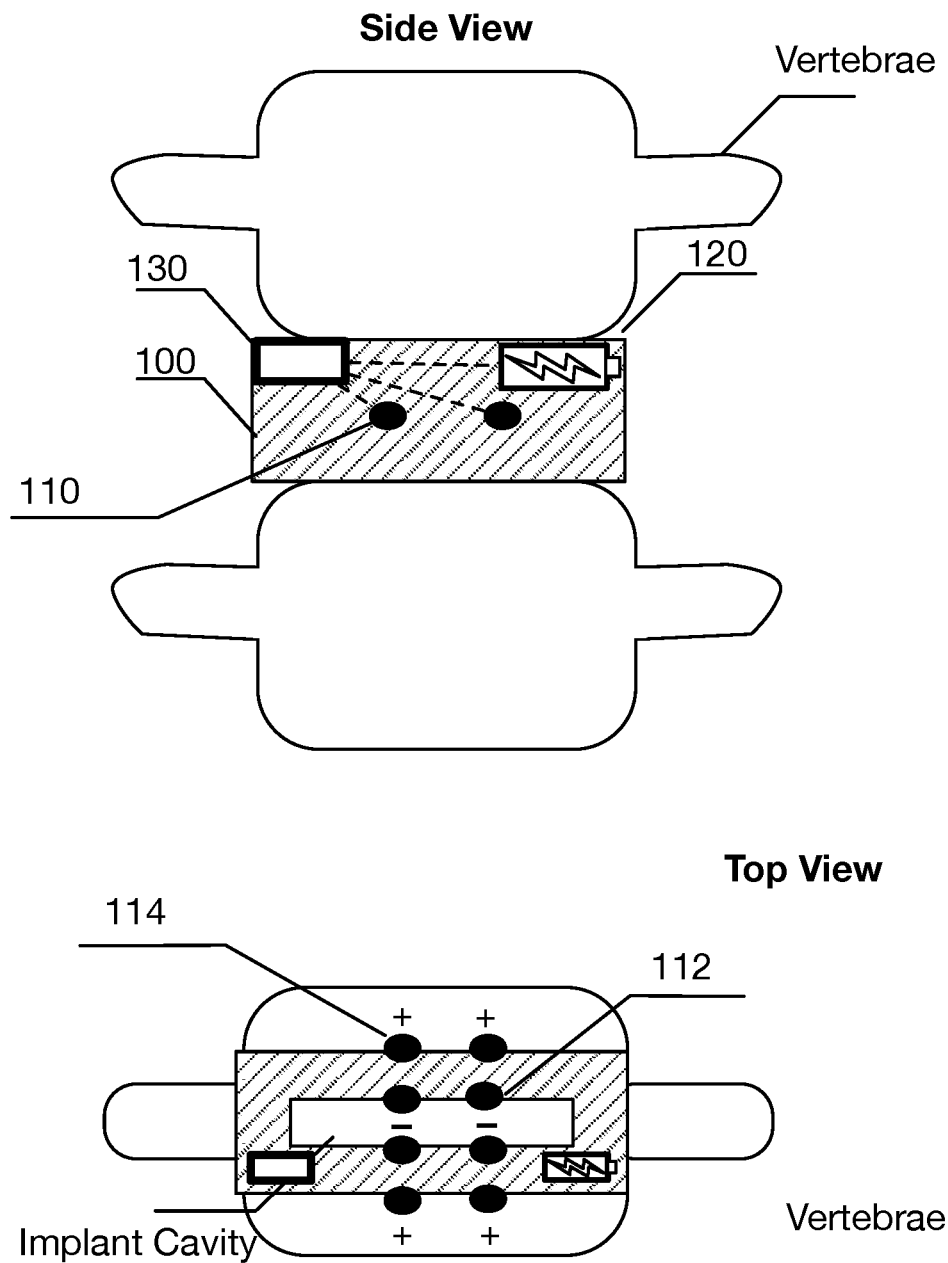
FIG. 2 is a second schematic representation of a system of a preferred embodiment.

As shown in FIG. 6, the lateral cage is another typically implemented spinal cage. The lateral cage is an implant body 100 with a large variance in size, and thus potentially large variance in implementation. In preferred variations, the lateral cage may only have a bone growth region in the interior cavity of the implant body 100. For this variation, the primary electrodes 112 may be along the interior surface of the lateral cage, while secondary electrodes 114 are along the exterior perimeter of the lateral cage. In one preferred example, as shown in FIG. 2, primary electrodes 112 include four electrodes exposed along the interior surface (e.g., two electrodes along the posterior interior surface and two electrodes along the anterior interior surface; and secondary electrodes 114 include four electrodes exposed on the exterior surface (e.g., two electrodes on the anterior surface and two electrodes on the posterior surface of the implant body 100). In one implementation all primary electrodes 112 function as cathodes to induce bone growth, while all secondary electrodes 114 function simultaneously as anodes. In a second implementation all primary electrodes 112 function as cathodes, while only a single secondary electrode 114 functions as anode at any given time. Over time, the active secondary electrode, functioning as the anode, cycles through all secondary electrodes to potentially minimize the osteolysis effects of the anode.

In a second variation, the system may include the primary electrodes along the interior surface of the implant body to induce bone growth, but alternatively the secondary electrodes 114 includes a single electrode distal to the bone growth region. In one example, the implant body 100 includes a metal casing, wherein the single secondary electrode is the metal casing of the implant body, as shown in FIG. 1. In a second example, the single secondary electrode 114 comprises an electrode on the "nose" of the implant body (i.e. the opposite side as the metal casing) as shown in FIG. 7.

In a third variation, as shown in FIG. 6, the system may further include a bone growth region on the posterior exterior of the implant body 100. This exterior bone growth region outside of the implant body 100 may be used to reduce bone growth in soft tissue. In this variation, the set of primary electrodes 112 includes electrodes along the interior surface and along the posterior, exterior surface of the implant body 100; and the set of secondary electrodes 114 includes electrodes along the exterior perimeter of the spinal cage, excluding the posterior surface of the implant body. In this variation, the primary electrodes 112 in the interior function primarily as cathodes, to induce bone growth; while the primary electrodes on the posterior surface function primarily as anodes (although occasionally as cathodes), to reduce bone growth on the posterior side of the implant body; and the secondary electrodes 114 may then function primarily as anodes to balance the required charge of the primary electrodes 112.

As shown in FIG. 10, the TLIF cage is another typically implemented spinal cage. The TLIF cage is an implant body 100 that is of "smaller" size, such that multiple TLIF cages may be implanted between a pair of vertebrae.

In one preferred variation, a single TLIF cage is implanted within the spinal region. In one example, wherein the TLIF cage is implanted fairly central in the spinal region, the bone growth region may include the interior cavity and the exterior region adjacent to the TLIF cage. In this example, primary electrodes 112 may be along both the interior surface and exterior surface of the implant body. In one implementation, secondary electrodes 114 may also be along the exterior surface of the TLIF cage. In this implementation, the control system 120 may activate the cyclical switching behavior of subsets of secondary electrodes 114 to prevent/reduce osteolysis in the exterior. In this implementation, the active subset of secondary electrodes 114 may change and circumnavigate the exterior surface of the implant body 100 to prevent significant bone loss in one region, enabling net bone growth external to the implant body 100.

In a second example of this variation, the secondary electrode 114 may comprise a single electrode extending out in one location from the implant body 100. This single electrode may lead to bone loss (or less bone growth) in that one region, with preferably little significant effect on other bone growth regions. In one implementation, wherein the TLIF cage is positioned such that the shorter end of the cage is pointing to the periphery of the spinal column, the secondary electrode 114 may be on the shorter end. In many implementations, less bone growth is needed as compared to other regions, positioning the secondary electrode 114 on the shorter end may thus minimize the significance of potential bone breakdown as compared to other regions.

In a second preferred variation, multiple TLIF cages (e.g., two TLIF cages) are implanted between a pair of vertebrae. In one example of this variation the two cages are fairly interior along the spinal column and this example functions similarly to the first variation.

In a second example of the second variation, the TLIF cages are implanted such that one side of each implant body is exterior to the bone growth region (e.g., outside of the spinal column). In this example, the system includes secondary electrodes 114 only along the exterior surface of the TLIF cage outside of the bone growth region, while the exterior surface of the implant body 100 within the bone growth region would include primary electrodes 112 along with the primary electrodes 112 within the implant body.

As shown in FIG. 9, the PLIF cage is another typically implemented spinal cage. The PLIF cage is an implant body 100 that is of "smaller" size, such that multiple PLIF cages may be implanted between a pair of vertebrae. As with the TLIF cage, a single PLIF cage or multiple PLIF cages may be implanted between each vertebra. Although insertion of the PLIF cage is from the posterior, implementations of the PLIF cage may be similar to the TLIF cage.

In one preferred variation, a single PLIF cage is implanted within the spinal region. In one example, wherein the PLIF cage is implanted fairly central in the spinal region, the bone growth region may include the interior cavity and the exterior region adjacent to the PLIF cage. In this example, primary electrodes 112 may be along both the interior surface and exterior surface of the implant body 100. In one implementation, secondary electrodes 114 may extend outwards from the exterior surface of the PLIF cage. In this implementation, the secondary electrodes 114 may extend sufficiently such that they don't affect the bone growth region.

In a second example of this variation, the secondary electrode 114 may comprise a single electrode extending out in one location from the implant body 100. This single electrode may lead to bone loss (or less bone growth) in that one region, with preferably little significant effect on other bone growth regions.

In a second preferred variation, multiple PLIF cages (e.g., two PLIF cages) are implanted between a pair of vertebrae. In one example of this variation, the two cages are fairly interior along the spinal column and this example functions similarly to the first variation.

In a second example of the second variation, the PLIF cages are implanted such that one side of each implant body is exterior to the bone growth region (e.g., outside of the spinal column). In this example, the system includes secondary electrodes 114 only along this exterior surface of the PLIF cage outside of the bone growth region, while the exterior surface of the implant body 100 within the bone growth region would include primary electrodes 112 along with the primary electrodes 112 within the implant body 100.

The ACF cage is another typically implemented spinal cage. The ACF cage may be a significantly smaller spinal cage wherein a single spinal cage is implanted between cervical vertebrae. Although typically much smaller, the ACF cage may have similar implementations as described for the ALIF cage.

In one preferred variation, the bone growth region of the ACF cage is the interior cavity of the implant body 100. For this variation, the primary electrodes 112 may be along the interior cavity of the ACF implant body 100, while secondary electrodes 114 are along the exterior perimeter of the implant body.

In an alternative variation, the ACF cage may additionally include a bone growth region directly exterior of the ACF cage perimeter. In this variation, primary electrodes 112 may additionally be along the anterior exterior surface of the implant body 100. Secondary electrodes 114 may include a single electrode extending outwards from the implant body 100, or may preferably include secondary electrodes 114 along the exterior surface of the implant body 110, wherein the secondary electrodes 114 alternate between active and not-active to minimize the undesired bone growth effects due to the secondary electrodes 114.

3. Method

As shown in FIG. 14, a method for altering bone growth on and within an orthopedic implant of a preferred embodiment includes: positioning electrodes S110, creating a polarity within a subset of electrodes S120. The method may function to create preferred regions of osteolysis and osteoinduction as desired by the polarity and positioning of the electrodes with respect to the implant. The method is preferably implemented with a system as described above, but may be implemented with any suitable alternative system.

Block S110, which includes positioning of electrodes, functions to set electrodes in specific spatial positions with respect to the implant where positioning of electrodes may designate possible regions of osteolysis or osteoinduction. Positioning of electrodes S110 may occur at different time within the method wherein the state of electrodes could be dynamically changed. Positioning of a subset of electrodes may or may not be dependent on the positioning of other subsets of electrodes. Positioning of a subset of electrodes may occur as described in U.S. patent application Ser. No. 15/075,152. Positioning of a subset of electrodes may occur prior to implantation of the implant, during the placement of the implant, after the implant has already been placed within a patient, and/or any combination of the prior, during, or after. Implants may have specific design features with electrode position in mind. For examples, implants may have holes or grooves for the placement of electrodes. Thus, positioning of a subset of electrodes may occur, or be determined, by the choice and/or design of the implant. Additionally or alternatively, a positioning of electrodes S110 may occur as desired.

Positioning of electrodes S110 may additionally be comprised of choosing the type of electrode. Choosing the electrode may include: choosing the composition, the size, and the shape of the electrode; as the material type(s), electrode thickness and surface area have an effect on the current passed through the electrode and generated electric field. If desired, a large surface area electrode may be used as an anode to balance the current generated from a large number of cathodes and which may ensure a low current density at the anode surface and the surrounding tissue.

Positioning of electrodes S110 may additionally be dependent on the shape of the electrodes. Wire-like, and/or arbitrarily shaped, but smaller electrodes may be preferably positioned within the implant, or within the implant cavities, but may alternatively be positioned in other regions, i.e. in, on, or outside of but proximal to the implant. Disc shaped, and/or large arbitrarily shaped electrodes, may preferably be positioned exterior to the implant. Additionally and/or alternatively, these larger electrodes may be positioned on or inside of the implant as is feasibly possible (e.g., large electrodes may not fit due to space). In one preferred variation, positioning of the electrode S110 additionally comprises of using the metal casing attached the implant as an electrode, as seen in FIG. 1. Alternatively and/or additionally, using the metal casing outside the implant may further require adding a metal casing to the implant. In another preferred variation, positioning of electrodes S110 may consist of positioning an electrode such that the electrode is adjacent to the implant with a shape that can cover the implant cavity, as in FIG. 6

Block S120, creating a polarity within a subset of electrodes functions in creating electro-positive electrodes and electro-negative electrodes that induce electric fields about each active electrode. Creating a polarity within a subset of electrodes S120 may function as described in U.S. patent application Ser. No. 15/075,152. The electro-negative electric fields may function in promoting osteoinduction while electro-positive electric fields may function in promoting osteolysis. Creating a polarity within a subset of electrodes S120 is preferably dependent on the specific layout of the system, the desired response in the patient, and the received biological response from the patient. Creating a polarity preferably includes creating a subset of electro-positive electrodes and creating a subset of electro-negative electrodes.

Creating a polarity within a subset of electrodes S120 preferably has at least two functions: stimulating bone material rearrangement (i.e. osteoinduction and osteolysis) and monitoring tissue composition. As described previously, osteoinduction/osteolysis activity may be stimulated by an electro-negative/positive environment. Thus, creating a polarity may create specific regions that haven enhance bone growth/decay.

Additionally, creating a polarity within a subset of electrodes S120 may enable monitoring tissue composition. Block S120, thus includes creating a polarity within subsets of electrodes using alternating current and measuring the impedance between the subsets of electrodes. Measuring the impedance between subsets of electrodes enables building an impedance profile about the implant and thus determine the tissue composition around and within the implant. Block S120 may be used in this manner to monitor the change in bone material between electrodes, and thus determine the amount of bone growth.

In preferred variations, monitoring tissue composition and stimulating bone material rearrangement happen in conjunction with each other. That is, the amount of bone material in a region is preferably utilized, to determine if, when, and how much stimulation should give be given to a region to stimulate bone growth or bone decomposition. From this point on, it is assumed that monitoring tissue composition is regularly implemented, and focus is given to the functionality of stimulating bone material rearrangement.

In creating a subset of electro-positive electrodes and creating a subset of electro-negative electrodes, the method creates regions of preferred osteolysis and osteoinduction, respectively. For the purpose of spinal fusion, generally speaking, creating a subset of electro-negative electrodes creates electro-negative regions near adjacent vertebrae such that the implant may fuse with the vertebrae. This region may include any interior cavity of the implant. Additionally creating a subset of electro-positive electrodes is preferably implemented far from these fusion sites and other sensitive areas (e.g., nerve tissue along the spinal column).

In one preferred example, wherein electrode rings are positioned as layers within the implant cavity, creating a polarity within a subset of electrodes S120 may comprise inducing the electrode rings to be cathodes in the highest and lowest rings, while middle ring(s) may become anodes; thereby potentially preventing osteolysis of the endplates as well as possibly stimulate bone growth in the endplate region.

In a preferred example, wherein the implant metal casing is used as an electrode. Creating a polarity within a subset of electrodes S120 may turn the metal casing into a positively charged electrode and thereby creating an osteolytic region directly outside of the implant. Having the metal casing positively charged electrode may additionally aid in reducing and/or removing all osteolytic regions within the implant or in the intervertebral space with the electropositive field being primarily located in the volume outside of the fusion site in the soft tissue surrounding the metal casing.

In a second preferred example, wherein electrodes extend out along the perimeter of the implant body, creating a polarity within a subset of electrodes S120 may turn a single electrode extending outwards from the implant into a positively charged electrode.

In a third preferred example, wherein electrodes extend out along the perimeter of the implant body, creating a polarity within a subset of electrodes S120 may cycle the activity of these electrodes. Subsets of the perimeter electrodes may be activated and positively charged, while other perimeter are completely inactive. After some time period, a new subset of perimeter electrodes may be activated and positively charged, while the previously charged subset of perimeter electrodes are made inactive. In this manner, the anode of the system may cycle through the set of perimeter electrodes while minimizing the effects of osteolysis in only one region.

As a person skilled in the art will recognize from the previous detailed description and from the figures and claims, modifications and changes can be made to the embodiments of the invention without departing from the scope of this invention as defined in the following claims.

We claim:

1. A system for altering bone growth on and within an orthopedic implant comprising:
   an implant body, wherein the implant body comprises an exterior surface and an interior surface defining an internal cavity of the implant body;
   a plurality of electrodes, wherein each electrode is at least partially embedded in the implant body, and comprises:
   a set of primary electrodes comprising at least one electrode, wherein a non-embedded segment of each primary electrode is proximal to a bone growth region including at least the defined internal cavity, the set of primary electrodes comprising at least two ring electrodes circumnavigating the defined internal cavity of the implant body, wherein one ring electrode circumnavigates the perimeter of the interior surface near the top of the internal cavity and the second ring electrode circumnavigates the perimeter of the interior surface near the bottom of the internal cavity,
   a set of secondary electrodes comprising at least one electrode, wherein a non-embedded segment of each secondary electrode is distal to the bone growth region, the set of secondary electrodes comprising at least one ring electrode circumnavigating the internal cavity near the middle of the internal cavity, and wherein the plurality of electrodes are configured to function in a stimulation operating mode, such that a subset of primary electrodes function as cathodes and a subset of secondary electrodes function as anodes;

a control system comprising a processor, and circuitry that connects to the plurality of electrodes, wherein the processor comprises machine instructions configured to control current traveling through each electrode from the plurality of electrodes.

2. The system of claim 1, wherein the set of secondary electrode comprises a single electrode distal to the bone growth region; and wherein the secondary electrode, in the stimulation operating mode functions as an electropositive source.

3. The system of claim 1, wherein the single electrode distal to the bone growth region comprises a metal casing of the implant body.

4. The system of claim 1, wherein the subset of secondary electrodes comprises the entire set of secondary electrodes.

5. The system of claim 1, wherein the subset of secondary electrodes comprises fewer electrodes than the entire set of secondary electrodes.

6. The system of claim 5, wherein the control system, during the stimulation operating mode, cycles through activation of distinct subsets of secondary electrodes, such that only a single subset of secondary electrodes function as electropositive sources at one time.

7. The system of claim 1, wherein the set of secondary electrodes comprises electrodes embedded in the implant body and exposed at the exterior surface of the implant body.

8. The system of claim 7, wherein: the implant body has a substantially rectangular prism shape, comprising a top surface, a bottom surface, two longer surfaces, and two shorter surfaces; and wherein, the set of secondary electrodes comprises at least four electrodes, with at least two electrodes exposed at electrode sites on each of the two longer exterior surfaces of the implant body.

9. The system of claim 1, wherein the control system in a monitoring mode is further configured to determine impedance through tissue, wherein the control system activates a pair of electrodes thereby running current through the intermediary tissue between the pair of electrodes, and determines the impedance due to the current dissipation between the pair of electrodes.

10. The system of claim 9, wherein the control system in a monitoring mode activates more than a pair of two electrodes.

11. The system of claim 10, wherein the control system, in a stimulation operation mode, modifies the activity of the plurality of electrodes in part from monitoring mode feedback.

12. The system of claim 1, wherein the implant body is a spinal cage.

13. The system of claim 12, wherein the spinal cage is an anterior lumbar interbody fusion cage.

14. The system of claim 13, wherein the set of primary electrodes comprises electrodes along the interior surface of the spinal cage, and the set of secondary electrodes comprises electrodes along the exterior lateral perimeter of the spinal cage.

15. The system of claim 12, wherein the spinal cage is a lateral cage.

16. The system of claim 15, wherein the set of primary electrodes comprises electrodes along the interior surface and along the posterior, exterior surface of the spinal cage; and the set of secondary electrodes comprises electrodes along the exterior perimeter of the spinal cage, excluding the posterior, exterior surface of the spinal cage.

17. The system of claim 12, wherein the spinal cage is a transforaminal lumbar interbody fusion cage.

18. The system of claim 17, wherein the set of primary electrodes comprises electrodes along the interior surface and the exterior surface of the spinal cage, and the set of secondary electrodes comprises a single electrode extending outward from the implant body; beyond the primary electrodes on the exterior surface.

19. The system of claim 17, wherein the set of primary electrodes comprises electrodes along the interior surface and the lateral exterior surface of the spinal cage, and the set of secondary electrodes comprises electrodes along the lateral exterior surface of the spinal cage.

20. The system of claim 12, wherein the spinal cage is a posterior lumbar interbody fusion (PLIF) cage, wherein the PLIF cage is implanted such that part of the lateral exterior surface of the spinal cage faces towards the spinal column and part of the lateral exterior surface of the spinal cage faces out from the spinal column; wherein the set of primary electrodes comprises of electrodes along the interior surface of the spinal cage and electrodes along lateral exterior surface of the spinal cage facing inwards; and the set of secondary electrodes comprises of electrodes along the lateral exterior surface of the spinal cage facing outwards.

21. The system of claim 12, wherein the spinal cage is an anterior cervical fusion (ACF) cage, wherein the set of primary electrodes comprise electrodes along the interior surface of the spinal cage, and the set of secondary electrodes comprise electrodes along the exterior lateral surface of the spinal cage.

* * * * *